(12) United States Patent
Kitagawa et al.

(10) Patent No.: US 9,310,389 B2
(45) Date of Patent: Apr. 12, 2016

(54) SAMPLE PROCESSING APPARATUS WITH SAMPLE FEEDING UNIT

(75) Inventors: Nobuhiro Kitagawa, Akashi (JP); Koichi Okubo, Kobe (JP)

(73) Assignee: Sysmex Corporation (JP)

( * ) Notice: Subject to any disclaimer, the term of this patent is extended or adjusted under 35 U.S.C. 154(b) by 458 days.

(21) Appl. No.: 12/883,561

(22) Filed: Sep. 16, 2010

(65) Prior Publication Data

US 2011/0065193 A1 Mar. 17, 2011

(30) Foreign Application Priority Data

Sep. 16, 2009 (JP) .................................. 2009-214489

(51) Int. Cl.
*G01N 35/02* (2006.01)
*G01N 35/04* (2006.01)
*G01N 35/00* (2006.01)

(52) U.S. Cl.
CPC .... *G01N 35/00732* (2013.01); *G01N 35/00613* (2013.01); *G01N 35/026* (2013.01); *G01N 35/04* (2013.01); *Y10T 436/11* (2015.01); *Y10T 436/114165* (2015.01)

(58) Field of Classification Search
None
See application file for complete search history.

(56) References Cited

U.S. PATENT DOCUMENTS

| 5,972,295 A | 10/1999 | Hanawa et al. |
| 6,290,907 B1 | 9/2001 | Takahashi et al. |
| 2008/0310999 A1 | 12/2008 | Yagi et al. |

FOREIGN PATENT DOCUMENTS

| JP | H11-148940 A | 6/1999 |
| JP | 11-304812 A | 11/1999 |
| JP | 2000-088861 A | 3/2000 |
| JP | 2000-131327 A | 5/2000 |
| JP | 2001-165752 A | 6/2001 |
| JP | 2003-57251 A | 2/2003 |

*Primary Examiner* — Yelena G Gakh
*Assistant Examiner* — Michelle Adams
(74) *Attorney, Agent, or Firm* — Brinks Gilson & Lione

(57) ABSTRACT

A sample processing apparatus including: a preprocessing unit for performing predetermined preprocessing on a sample container; a transporting unit for transporting the sample container on which the preprocessing unit has performed the predetermined preprocessing; a sample processing unit for processing a sample contained in the sample container transported by the transporting unit; a plurality of container collection units for collecting respective sample containers transported by the transporting unit; and a collection controller for controlling, according to a result of the predetermined preprocessing by the preprocessing unit, at least one of the transporting unit and the plurality of container collection units such that the sample container transported by the transporting unit is collected in one of the plurality of container collection units.

12 Claims, 20 Drawing Sheets

SAMPLE PROCESSING APPARATUS WITH SAMPLE FEEDING UNIT

RELATED APPLICATIONS

This application claims priority under 35 U.S.C. §119 to Japanese Patent Application No. 2009-214489 filed on Sep. 16, 2009, the entire content of which is hereby incorporated by reference.

BACKGROUND OF THE INVENTION

Conventionally, there is a known sample processing apparatus capable of transporting a sample rack that holds multiple sample containers to a sample processing unit such as a blood analyzer, and processing samples contained in the sample containers held by the sample rack by means of the sample processing unit (e.g., blood analysis).

U.S. Pat. No. 5,972,295 discloses a sample testing system that includes: an analysis part for performing sample analysis; a transport line for transporting a sample rack to the analysis part; a rack supply part for supplying the transport line with a sample rack that has been fed by a user; a rack collection part for collecting and storing a sample rack for which analysis has been performed by the analysis part; a standby part for receiving, from the transport line, the sample rack for which the analysis has been performed by the analysis part and provisionally accommodating the sample rack; a control section for determining whether or not the sample rack accommodated in the standby part requires retesting; and a distribution switching part for distributing, among sample racks, a sample rack that requires retesting to the return line and a sample rack that does not require retesting to the rack collection part. In the sample testing system disclosed in U.S. Pat. No. 5,972,295, a sample rack that does not require retesting is collected in the rack collection part without being transported to the return line, and a sample rack that requires retesting is transported by the return line to the entrance of the transport line, and then transported to the analysis part by the transport line again. Thereafter, the sample rack is collected in the rack collection part.

However, in the sample testing system disclosed by U.S. Pat. No. 5,972,295, all the sample racks fed by a user are eventually stored by the rack collection part. Accordingly, the sample racks having been collected in the rack collection part include a sample rack holding samples that have been tested properly, a sample rack holding samples that are to be retested by an apparatus different from the analysis part of the system, a sample rack holding samples that have not been tested due to errors in sample bar code reading, etc. For this reason, a user is required to separate the sample racks collected in the rack collection part in order to send the sample racks to their respective following steps (e.g., discarding, storing, retesting by a different apparatus, and re-affixing of bar code labels). Thus, the burden is greatly imposed on the user.

SUMMARY OF THE INVENTION

The scope of the present invention is defined solely by the appended claims, and is not affected to any degree by the statements within this summary.

A first aspect of the present invention is a sample processing apparatus comprising: a preprocessing unit for performing predetermined preprocessing on a sample container; a transporting unit for transporting the sample container on which the preprocessing unit has performed the predetermined preprocessing; a sample processing unit for processing a sample contained in the sample container transported by the transporting unit; a plurality of container collection units for collecting respective sample containers transported by the transporting unit; and a collection controller for controlling, according to a result of the predetermined preprocessing by the preprocessing unit, at least one of the transporting unit and the plurality of container collection units such that the sample container transported by the transporting unit is collected in one of the plurality of container collection units.

A second aspect of the present invention is a sample processing apparatus comprising: a transporting unit for transporting a sample container that contains a sample; a measurement unit for measuring the sample contained in the sample container transported by the transporting unit; an analysis result obtaining unit for obtaining an analysis result of the sample that is based on a result of the measurement performed by the measurement unit; a plurality of container collection units for collecting respective sample containers transported by the transporting unit; and a collection controller for controlling, according to the analysis result obtained by the analysis result obtaining unit, at least one of the transporting unit and the plurality of container collection units such that the sample container transported by the transporting unit is collected in one of the plurality of container collection units.

A third aspect of the present invention is a sample processing apparatus comprising: a sample feeding unit in which pre-tested racks each holding at least one sample container therein is storable, the sample feeding unit being configured to interrogate a respective at least one sample container held in the respective pre-tested racks to read attribute information therefrom; a testing unit configured to test a respective sample in one or more of the at least one sample container held in a pre-tested rack and issue a test result on the respective sample, the attribute information being determinable of a type of test requested to be performed by the testing unit; a plurality of collecting units for storing post-tested racks, wherein the test result, as well as the attribute information, is determinative of a collecting unit, from among the plurality of collecting units, to which the respective post-tested racks is to be transported; and a transport apparatus configured to transport the pre-tested rack to the testing unit and the respective post-tested racks to a selected one of the plurality of collecting units.

A fourth aspect of the present invention is a sample processing method comprising: performing predetermined preprocessing on a sample container; transporting, by a transporting unit, the sample container on which the predetermined preprocessing has been performed; processing a sample contained in the sample container transported by the transporting unit; and collecting the sample container transported by the transporting unit, by one of a plurality of container collection units according to a result of the predetermined preprocessing.

DETAILED DESCRIPTION OF THE PREFERRED EMBODIMENTS

Hereinafter, preferred embodiments of the present invention will be described with reference to the drawings.

First Embodiment

A first embodiment of the present invention is a sample processing apparatus that includes: a feeding unit for feeding a sample rack that accommodates multiple samples; a preprocessing unit for reading a sample bar code affixed to each sample held by the sample rack which has been fed; transporting apparatuses for transporting the sample rack which has been fed; a blood analyzer; and a first collection unit and a second collection unit for collecting respective sample racks that are transported thereto through the blood analyzer. The sample processing apparatus collects sample racks separately by the first collection unit and the second collection unit in accordance with a result of the preprocessing unit having read sample bar codes. Moreover, the sample processing apparatus collects sample racks separately by the first collection unit and the second collection unit in accordance with results of analysis performed by the blood analyzer.

[Configuration of Sample Processing Apparatus]

Figure 1:
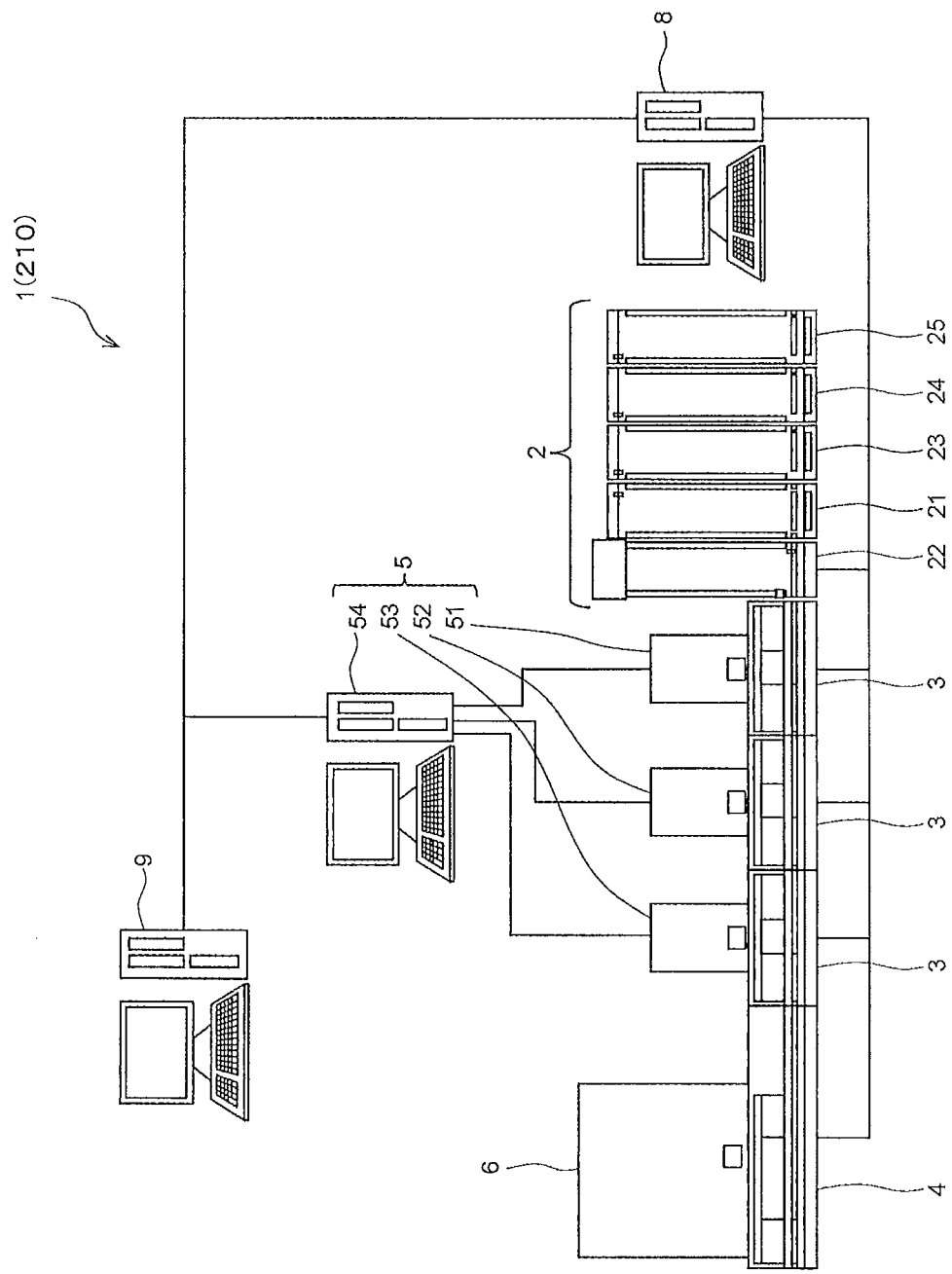
FIG. 1 is a schematic plan view showing the entire configuration of a sample processing apparatus according to a first embodiment.

FIG. 1 is a schematic plan view showing the entire configuration of a sample processing apparatus according to the present embodiment. As shown in FIG. 1, a sample processing apparatus 1 includes a sample feeding/collecting apparatus 2, sample transporting apparatuses 3 and 4, a blood cell analyzer 5, a smear preparing apparatus 6, and a system control apparatus 8. The sample processing apparatus 1 according to the present embodiment is communicably connected to a laboratory test information management apparatus 9 via a communication network.

<Configuration of Sample Feeding/Collecting Apparatus 2>

Figure 2:
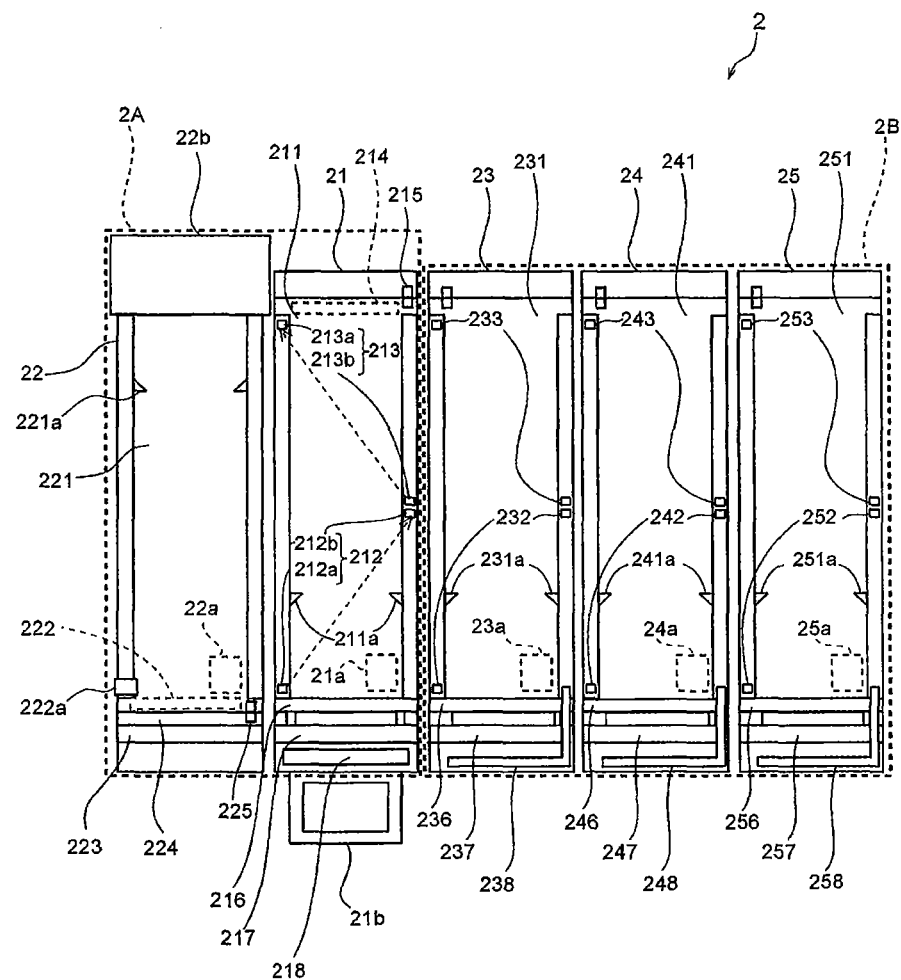
FIG. 2 is a plan view showing a configuration of a sample feeding/collecting apparatus according to the first embodiment.

FIG. 2 is a plan view showing a configuration of the sample feeding/collecting apparatus 2 according to the present embodiment. The sample feeding/collecting apparatus 2 includes a sample feeding unit 21, a preprocessing unit 22, and sample collection units (rack collection parts) 23, 24 and 25. Sample racks each accommodating multiple sample containers can be mounted in the sample feeding/collecting apparatus 2. The sample feeding/collecting apparatus 2 has a sample feeding unit group 2A which includes the sample feeding unit 21 and the preprocessing unit 22, and a sample collection unit group 2B which includes the sample collection units 23, 24, and 25.

Figure 3:
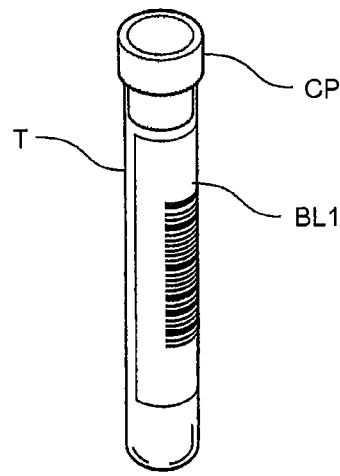
FIG. 3 is a perspective view showing an external view of a sample container.
Figure 4:
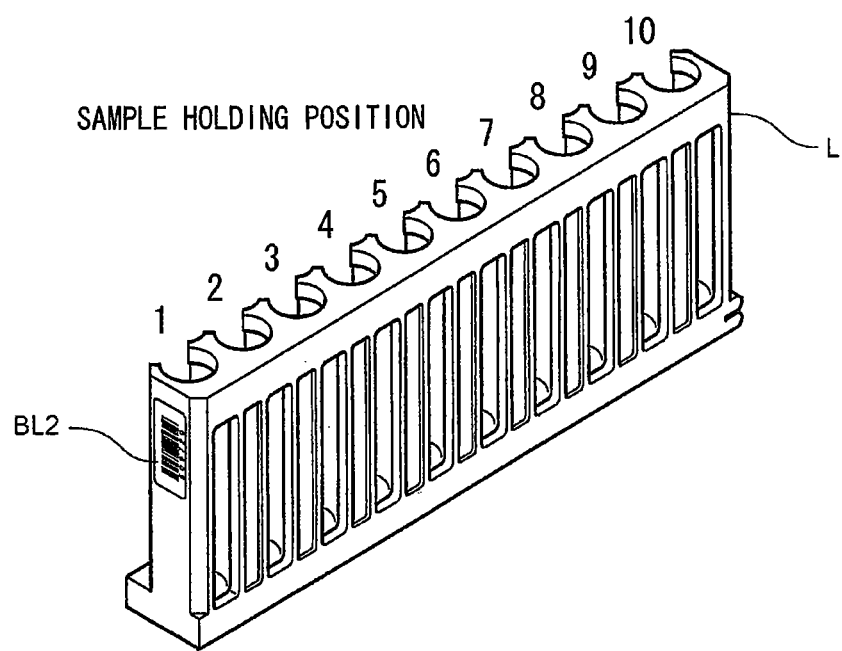
FIG. 4 is a perspective view showing an external view of a sample rack.

FIG. 3 is a perspective view showing an external view of a sample container. FIG. 4 is a perspective view showing an external view of a sample rack. As shown in FIG. 3, a sample container T has a tubular shape and the upper end thereof has an opening. The sample container T contains a blood sample collected from a patient, and the opening at the upper end is sealed with a cap CP. The sample container T is formed of a glass having translucency or a synthetic resin so that the blood sample contained therein can be viewed from the outside. A bar code label BL1 is affixed to the side of the sample container T. On the bar code label BL1, a bar code (a sample bar code) representing a sample ID is printed. A sample rack L is configured to hold ten sample containers T in a line. Each sample container T is held vertically (i.e., in a standing position) in the sample rack L. A bar code label BL2 is affixed to one of the sides of the sample rack L. On the bar code label BL2, a bar code representing a rack ID (a rack bar code) is printed.

Referring to FIG. 2, the sample feeding unit 21 has a rack mounting part 211 which is U-shaped in cross section. The rack mounting part 211 allows sample racks L each accommodating sample containers T to be mounted therein. The rack mounting part 211 has a rectangular shape, and multiple sample racks L can be mounted in the rack mounting part 211 at the same time. Here, each sample rack L is mounted in the rack mounting part 211 such that the accommodated sample containers T are arranged laterally. The rack mounting part 211 is provided with sensors 212 and 213 each for detecting a sample rack L and with engagement portions 211a for moving the sample rack L. The sensors 212 and 213 are optical sensors. The sensor 212 includes a light emitter 212a and a light receiver 212b, and the sensor 213 includes a light emitter 213a and a light receiver 213b. The light emitter 212a is disposed at the front left side of the rack mounting part 211, and the light receiver 212b is disposed at the center, with respect to the front-rear directions, of the right side of the rack mounting part 211. The light emitter 213a is disposed at the rear left side of the rack mounting part 211. The light receiver 213b is disposed at the center, with respect to the front-rear directions, of the right side of the rack mounting part 211. The light emitter 212a is disposed such that light emitted therefrom travels diagonally backward to the right. The light receiver 212b is disposed so as to receive the light after the light has traveled across the rack mounting part 211. The light emitter 213a is disposed such that light emitted therefrom travels diagonally forward to the right. The light receiver 213b is disposed so as to receive the light after the light has traveled across the rack mounting part 211. Accordingly, when a sample rack L mounted in the rack mounting part 211 blocks the light emitted from the light emitter 212a or 213a, causing a decrease in the light reception level of the light receiver 212b or 213b, the sample rack L is detected by the rack sensor 212 or 213. The sample rack L detected by the rack sensor 212 or 213 is then engaged by the engagement portions 211a. The engagement portions 211a engaging the sample rack L move backward. As a result, the sample rack L is moved within the rack mounting part 211.

The innermost (rearmost) position of the rack mounting part 211 is a rack send-out position 214 at which a sample rack L is sent out from the sample feeding unit 21 to the left. A protruding portion 215 movable to the right and left is provided at the rack send-out position 214. The protruding portion 215 remains idle at a position near the right end of the rack send-out position 214 until a sample rack L is moved to the rack send-out position 214. When a sample rack L arrives at the rack send-out position 214, the protruding portion 215 moves to the left. Accordingly, the sample rack L is pushed by the protruding portion 215 and moved to the left. There is no wall at the right and left sides of the rack send-out position 214. Accordingly, the sample rack L pushed by the protruding portion 215 is sent out from the sample feeding unit 21. As shown in FIG. 2, the preprocessing unit 22 is provided at the left side of the sample feeding unit 21. The preprocessing unit 22 has a right side wall which has an open portion through which the sample rack L sent out from the rack send-out position 214 enters the preprocessing unit 22.

A first transport line 216 and a second transport line 217 which are parallel belt conveyers are provided at the front of the rack mounting part 211. The sample feeding unit 21 has walls at the right and left sides of the rack mounting part 211, the walls having open portions at the right and left sides of the first and second transport lines 216 and 217. This allows a sample rack L to be transported onto the first transport line 216 or the second transport line 217, and then from the first transport line 216 or the second transport line 217 to another unit. The inner bottom surface of the rack mounting part 211, the first transport line 216, and the second transport line 217 are disposed at the same height, thereby forming a substantially even surface. The sample feeding unit 21 is provided with a rack moving part 218 for moving backward a sample rack L that has been transported onto the first transport line 216 or the second transport line 217. The rack moving part 218 is a rod-shape member that is horizontally long. The rack moving part 218 is movable forward and backward within a range in the front-rear direction from the second transport line 217 to the central position of the rack mounting part 211. If the rack moving part 218 moves backward from a position at the front of a sample rack L that has been transported onto the first transport line 216 or the second transport line 217, then the rack moving part 218 comes in contact with the front face of the sample rack L. If the rack moving part 218 moves further backward, the sample rack L is pushed and moved backward, accordingly. As a result, the sample rack L is moved backward to a position beyond the engagement portions 211a. Thereafter, the sample rack L is moved by the engagement portions 211a to the rack send-out position 214. As described above, the sample feeding unit 21 is configured to send a sample rack L that has been transported thereto by the first transport line 216 or the second transport line 217 into the sample collection unit 23 disposed at the right side of the sample feeding unit 21, and to move a sample rack L that is present on the first transport line 216 or the second transport line 217 to the rack send-out position 214, and then send the sample rack L into the preprocessing unit 22 disposed at the left side of the sample feeding unit 21.

The sample feeding unit 21 having the above configuration includes a controller 21a that includes a CPU, memory, and the like. The controller 21a controls the mechanics of the sample feeding unit 21. The sample feeding unit 21 includes an Ethernet (registered-trademark) interface that is communicably connected to an information processing unit 54 and the system control apparatus 8 via a LAN. The sample feeding unit 21 is provided with an operation panel 21b. By operating the operation panel 21b, the user can instruct the sample processing apparatus 1 to start or end sample processing.

The preprocessing unit 22 is connected to the left side of the sample feeding unit 21. A sample rack L sent out from the rack send-out position 214 to the left enters the preprocessing unit 22. The preprocessing unit 22 includes a rack mounting part 221 configured to accommodate multiple sample racks L, the rack mounting part 221 having a quadrangle shape when seen in plan view. The preprocessing unit 22 includes a bar code reader 22b at the rear side of the rack mounting part 221. The bar code reader 22b is configured to read, at the same time, the sample bar codes of multiple sample containers T accommodated in a sample rack L, and to read the rack bar code of the sample rack L. The bar code reader 22b is provided with an optical sensor (not shown) for detecting a sample container T. When a sample rack L arrives at a bar code reading position of the bar code reader 22b, the optical sensor detects the presence or absence of sample containers T. The bar code reader 22b includes a horizontal rotation mechanism (not shown) for horizontally rotating multiple sample containers T at the same time. The horizontal rotation mechanism is provided at the innermost side of the rack mounting part 221, immediately above the bar code reading position. A sample rack L sent out from the rack send-out position 214 of the sample feeding unit 21 to the left enters the preprocessing unit 22, and then arrives at the bar code reading position. Thereafter, sample containers T accommodated in the sample rack L are horizontally rotated by the horizontal rotation mechanism. While the sample containers T are being horizontally rotated, the bar code reader 22b reads sample IDs from the bar code labels BL1 of the sample containers T, and reads a rack ID from the bar code label BL2 of the sample rack L.

When a sample rack L arrives at the bar code reading position, the aforementioned optical sensor detects the presence of sample containers T and the bar code reader 22b reads the sample bar code of each sample container T multiple times consecutively. When data of sample IDs read from the multiple readings, respectively, coincide between the multiple readings, the sample bar code reading is determined to be successful. Sample IDs and a rack ID, which have been read, are transmitted to the system control apparatus 8. In the detection of a sample container T by the optical sensor, if there is no single sample bar code having been read during a predetermined time period, or if data of a sample bar code that has been read multiple times during the predetermined time period is not constant among the multiple readings, or if a sample bar code has been read only once during the predetermined time period, the sample bar code reading is determined to have failed. If the bar code reading has failed for a sample, a controller 22a of the preprocessing unit 22 transmits to the system control apparatus 8 sample bar code reading error information associated with a sample holding position of the sample rack L, in which position the sample is being held.

The inner surfaces of the right and left walls of the rack mounting part 221 have respective engagement portions 221a protruding therefrom. The engagement portions 221a engage a sample rack L for which sample bar codes and a rack bar code have been read by the bar code reader 22b, and then move forward. Accordingly, the sample rack L moves forward within the rack mounting part 221. The frontmost position of the rack mounting part 221 is a rack send-out position 222. A transport line 223 which is a belt conveyer is provided at the front of the rack send-out position 222. A wall-like partition 224 protrudes between the transport line 223 and the rack send-out position 222. The partition 224 includes a protruding portion 225 that is movable to the right and left. The protruding portion 225 remains idle at a position near the right end of the rack send-out position 222 until a sample rack L is moved to the rack send-out position 222. When a sample rack L has arrived at the rack send-out position 222, the protruding portion 225 moves to the left. Accordingly, the sample rack L is pushed by the protruding portion 225 and moved to the left. There is no wall at the right and left sides of the rack send-out position 222. Accordingly, the sample rack L pushed by the protruding portion 225 is sent out from the preprocessing unit 22. As shown in FIG. 1, one of the sample transporting apparatuses 3 is connected to the left side of the preprocessing unit 22. The rack send-out position 222 aligns with below-described overtaking lines (rack overtaking transporters) of the sample transporting apparatuses 3. Accordingly, the sample rack L sent out from the rack send-out position 222 enters the overtaking line of the adjacent sample transporting apparatus 3.

Near the rack send-out position 222, a bar code reader 222a for reading a rack bar code is provided. The bar code reader 222a reads the rack ID of a sample rack L that has been moved to the rack send-out position 222. The read rack ID is transmitted to the system control apparatus 8. As described below, the system control apparatus 8 receives the rack ID, thereby determining a transportation destination of the sample rack L to be transported.

There is no wall at the right and left sides of the transport line 223. The transport line 223 aligns with below-described return lines (rack returning transporters) of the sample transporting apparatuses 3 and the aforementioned second transport line 217 of the sample feeding unit 21. Accordingly, the transport line 223 receives a sample rack L from the return line of the adjacent sample transporting apparatus 3, and transports the sample rack L onto the second transport line 217 of the sample feeding unit 21.

The preprocessing unit 22 having the above configuration includes the controller 22a that includes a CPU, memory, and the like. The controller 22a controls the mechanics of the preprocessing unit 22. The preprocessing unit 22 includes an Ethernet (registered-trademark) interface that is communicably connected to the information processing unit 54 and the system control apparatus 8 via the LAN.

The sample collection units 23, 24, and 25 are arranged side-by-side at the right side of the sample feeding unit 21. The sample feeding unit 21 is connected to the sample collection unit 23 which is disposed at the leftmost position among the sample collection units 23, 24, and 25. Each of the sample collection units 23, 24, and 25 has the same configuration as that of the sample feeding unit 21. That is, the sample collection units 23, 24, and 25 include: rack mounting parts 231, 241, and 251, each of which is U-shaped in cross section and allows a sample rack L to be mounted therein; engagement portions 231a, 241a, and 251a for moving respective sample racks L backward that are mounted in the rack mounting parts 231, 241, and 251; sensors 232, 233, 242, 243, and 252, 253 for detecting sample racks L; first transport lines 236, 246, and 256, provided at the front of the rack mounting parts 231, 241, and 251, respectively, for laterally transporting respective sample racks L; second transport lines 237, 247, and 257, provided at the front of the rack mounting parts 231, 241, and 251, respectively, for laterally transporting respective sample racks L; and rack moving parts 238, 248, and 258 for moving respective sample racks L that have been transported onto the first transport lines 236, 246, and 256 or onto the second transport lines 237, 247, and 257 to the rack mounting parts 231, 241, and 251. The sample collection units 23, 24, and 25 are connected such that the first transport lines 236, 246, and 256 align with each other and the second transport lines 237, 247, and 257 align with each other.

The sample collection units 23, 24, and 25 include controllers 23a, 24a, and 25a, respectively. Each of the controllers 23a, 24a, and 25a includes a CPU, memory, and the like. The controllers 23a, 24a, and 25a control the mechanics of the sample collection units 23, 24, and 25, respectively. Each of the sample collection units 23, 24, and 25 includes an Ethernet (registered-trademark) interface that is communicably connected to the information processing unit 54 and the system control apparatus 8 via the LAN.

The sample collection units 23, 24, and 25 collect respective sample racks L that have been transported thereto through measurement units 51, 52, and 53 of the blood cell analyzer 5 or through the smear preparing apparatus 6. The sample racks L are separately collected in accordance with respective purposes of steps that are to be performed on the respective sample racks L after the collection. The sample collection unit 25 is used for collecting a sample rack L that accommodates only sample containers T for which preprocessing, i.e., sample bar code reading in the present embodiment, has been properly performed, and for which analysis of contained samples has been properly performed, and for which retesting of the contained samples is not necessary. The sample collection unit 24 is used for collecting a sample rack L that accommodates sample containers T that include a sample container T for which the preprocessing (sample bar code reading) has been properly performed, and for which analysis of a contained sample has been properly performed, and for which retesting of the contained sample is necessary due to the analysis results. The sample collection unit 23 is used for collecting a sample rack L that accommodates sample containers T that include a sample container T for which the preprocessing (sample bar code reading) has failed and for which analysis of a contained sample has not been performed by the blood cell analyzer 5, and for collecting a sample rack L that accommodates sample containers T that include a sample container T for which analysis of a contained sample has not been performed by the blood cell analyzer 5 due to malfunction of the blood cell analyzer 5.

<Configurations of Sample Transporting Apparatuses 3>

Next, configurations of the sample transporting apparatuses 3 are described. As shown in FIG. 1, the sample processing apparatus 1 includes three sample transporting apparatuses 3. The three sample transporting apparatuses 3 are disposed at the front of the three measurement units 51, 52, and 53 of the blood cell analyzer 5, respectively. Adjoining sample transporting apparatuses 3 are connected to each other so that they can send/receive a sample rack L to/from each other. Among the sample transporting apparatuses 3, the rightmost sample transporting apparatus 3 is connected to the above-described sample feeding/collecting apparatus 2. This allows the rightmost sample transporting apparatus 3 to receive a sample rack L transported from the sample feeding/collecting apparatus 2 and send out a sample rack L from the rightmost sample transporting apparatus 3 to the sample feeding/collecting apparatus 2.

Figure 5:
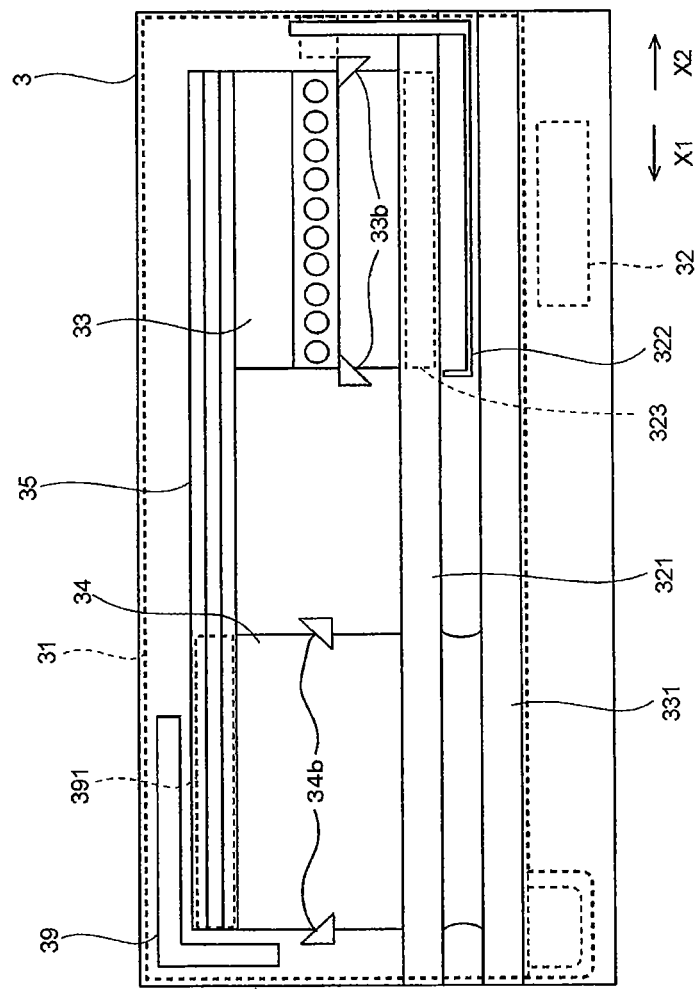
FIG. 5 is a plan view showing a configuration of each sample transporting apparatus used for a blood analyzer according to the first embodiment.

FIG. 5 is a plan view showing a configuration of each sample transporting apparatus 3. Although, among the sample transporting apparatuses 3, only the sample transporting apparatus 3 that corresponds to, i.e., that is disposed at the front of, the measurement unit 51 is described here, the sample transporting apparatuses 3 that correspond to, i.e., that are disposed at the front of, the measurement units 52 and 53, respectively, have the same configuration as that of the sample transporting apparatus 3 that is disposed at the front of the measurement unit 51. As shown in FIG. 5, the sample transporting apparatus 3 includes a transporting mechanism 31 for transporting samples and a controller 32 for controlling the transporting mechanism 31. The transporting mechanism 31 includes: an unanalyzed rack holder 33 configured to temporarily hold a sample rack L that accommodates sample containers T containing samples that have not been analyzed; an analyzed rack holder 34 configured to temporarily hold a sample rack L that accommodates sample containers T from which samples have been aspirated by the corresponding measurement unit 51; a rack transporter 35 configured to horizontally and linearly move a sample rack L in an arrow X1 direction as indicated in FIG. 5, so as to transport a sample rack L received from the unanalyzed rack holder 33 to the analyzed rack holder 34 for the purpose of supplying samples to the measurement unit 51; a rack overtaking transporter 321 for receiving a sample rack L from an upstream apparatus (hereinafter, the term "upstream" refers to "upstream" in relation to the transporting direction which is the X1 direction, and the term "downstream" refers to "downstream" in relation to the transporting direction), that is, the sample feeding/collecting apparatus 2 (or in the case of the other sample transporting apparatuses 3, the adjacent upstream sample transporting apparatus 3), and for transporting the sample rack L to a downstream apparatus, that is, the adjacent downstream sample transporting apparatus 3 (or in the case of the sample transporting apparatus 3 disposed at the front of the measurement unit 53, the sample transporting apparatus 4) without supplying samples accommodated in the sample rack L to the measurement unit 51; and a rack returning transporter 331 for receiving a sample rack L from a downstream apparatus, that is, the adjacent downstream sample transporting apparatus 3 (or in the case of the sample transporting apparatus 3 disposed at the front of the measurement unit 53, the sample transporting apparatus 4), and for transporting the sample rack L to an upstream apparatus, that is, the sample feeding/collecting apparatus 2 (or in the case of the other sample transporting apparatuses 3, the adjacent upstream sample transporting apparatus 3) without supplying samples accommodated in the sample rack L to the measurement unit 51.

The controller 32 includes a CPU, a ROM, a RAM, and the like (not shown). The CPU of the controller 32 is configured to execute a control program stored in the ROM for controlling the transporting mechanism 31. The controller 32 includes an Ethernet (registered-trademark) interface that is communicably connected to the information processing unit 54 and the system control apparatus 8 via the LAN.

The sample transporting apparatus 3 transports, to an unanalyzed rack send-out position 323 by means of the rack overtaking transporter 321, a sample rack L that has been transported from the sample feeding/collecting apparatus 2 to the sample transporting apparatus 3. Then, the sample transporting apparatus 3 moves the sample rack L to the unanalyzed rack holder 33 by means of a rack send-out part 322, and sends the sample rack L from the unanalyzed rack holder 33 to the rack transporter 35 by means of a rack send-in part 33b. The sample transporting apparatus 3 further transports the sample rack L by means of the rack transporter 35 to the corresponding measurement unit 51 of the blood cell analyzer 5, thereby supplying samples to the corresponding measurement unit 51. A sample rack L that accommodates sample containers from which samples have been aspirated is moved by the rack transporter 35 to an analyzed rack send-out position 391, and sent out to the analyzed rack holder 34 by a rack send-out part 39. A sample rack L held by the analyzed rack holder 34 is moved to the rack overtaking transporter 321 if samples held in the sample rack L need to be measured by the downstream measurement unit 52 or 53, or need to be supplied for smear preparation by the smear preparing apparatus 6. The sample rack L is then transported by the rack overtaking transporter 321 to an apparatus disposed subsequent to (i.e., adjacent to and downstream from) the sample transporting apparatus 3, that is, the subsequent sample transporting apparatus 3 (or in the case of the sample transporting apparatus 3 disposed at the front of the measurement unit 53, the sample transporting apparatus 4). If none of the samples accommodated in the sample rack L held by the analyzed rack holder 34 need to be measured by the downstream measurement unit 52 or 53, or need to be supplied for smear preparation by the smear preparing apparatus 6, then the sample rack L is moved to the rack returning transporter 331. The rack returning transporter 331 transports the sample rack L to an apparatus disposed preceding (i.e., adjacent to and upstream from) the sample transporting apparatus 3, that is, the sample feeding/collecting apparatus 2 (or in the case of the other sample transporting apparatuses 3, the preceding sample transporting apparatus 3). If the sample transporting apparatus 3 has received from the preceding apparatus a sample rack L that accommodates samples to be processed by the downstream measurement unit 52, 53, or the downstream smear preparing apparatus 6, then the sample rack L is transported in the arrow X1 direction by the rack overtaking transporter 321 to the subsequent sample transporting apparatus 3 (or in the case of the sample transporting apparatus 3 disposed at the front of the measurement unit 53, the sample transporting apparatus 4). On the other hand, if the sample transporting apparatus 3 has received from the subsequent apparatus a sample rack L to be collected by the sample feeding/collecting apparatus 2, the sample rack L is transported in the arrow X2 direction by the rack returning transporter 331 to the sample feeding/collecting apparatus 2 (or in the case of the other sample transporting apparatuses 3, the preceding sample transporting apparatus 3).

Note that, among the components of the transporting mechanism 31, the rack send-in part 33b, the rack transporter 35, and the rack send-out part 39 are controlled by the information processing unit 54 of the blood cell analyzer 5. The other components of the transporting mechanism 31 are controlled by the controller 32.

<Sample Transporting Apparatus 4>

As shown in FIG. 1, the sample transporting apparatus 4 is disposed at the front of the smear preparing apparatus 6. The sample transporting apparatus 3 that is disposed most downstream in the transporting direction among the three sample transporting apparatuses 3 (i.e., the leftmost sample transporting apparatus 3 in FIG. 1) is connected to the right end of the sample transporting apparatus 4.

Figure 6:
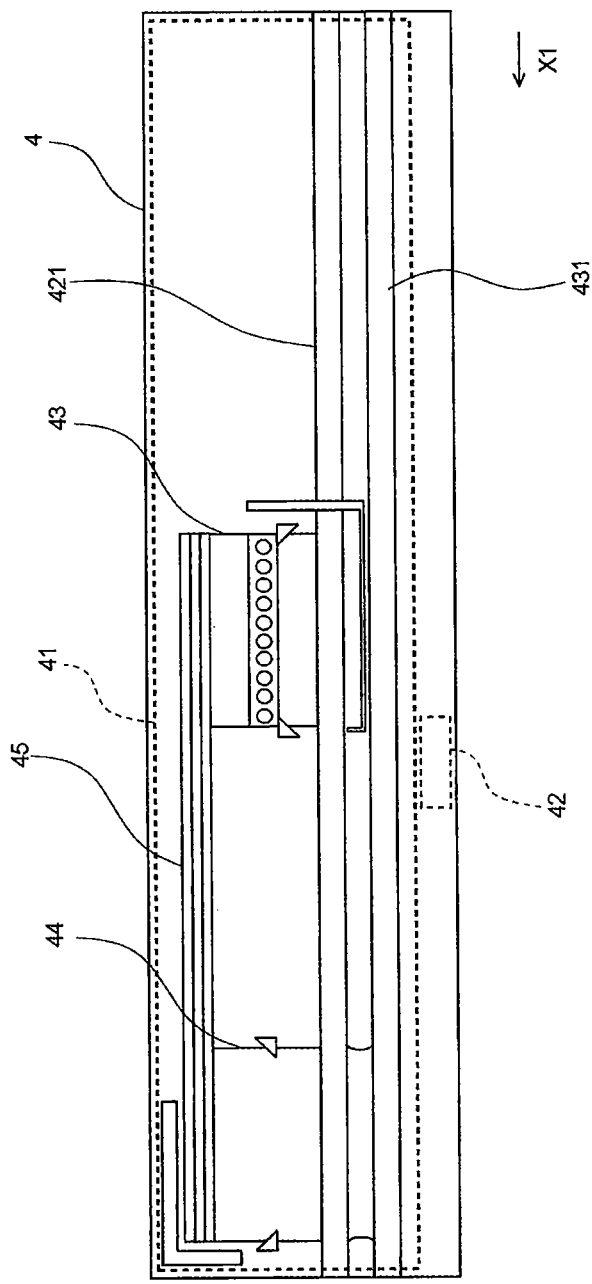
FIG. 6 is a plan view showing a configuration of a sample transporting apparatus used for a smear preparing apparatus according to the first embodiment.

FIG. 6 is a plan view showing a configuration of the sample transporting apparatus 4. The sample transporting apparatus 4 includes a transport mechanism 41 for transporting samples and a controller 42 for controlling the transport mechanism 41. The transport mechanism 41 includes: an unprocessed rack holder 43 configured to temporarily hold a sample rack L that accommodates sample containers T containing samples that have not yet been used for smear preparation; a processed rack holder 44 configured to temporarily hold a sample rack L that accommodates sample containers T from which samples have been aspirated by the smear preparing apparatus 6; a rack transporter 45 for horizontally and linearly moving a sample rack L in the X1 direction so as to transport a sample rack L received from the unprocessed rack holder 43 to the processed rack holder 44 for the purpose of supplying samples to the smear preparing apparatus 6; a rack overtaking transporter 421 for receiving a sample rack L from the adjacent upstream sample transporting apparatus 3 and transporting the sample rack L in the X1 direction; and a rack returning transporter 431 for transporting a sample rack L for which smear preparation using samples accommodated in the sample rack L has been completed to the adjacent upstream sample transporting apparatus 3, for the purpose of causing the sample rack L to be collected by the sample feeding/collecting apparatus 2. The sample transporting apparatus 4 is different from the sample transporting apparatus 3 in terms of the sizes, shapes, and positions of the components. However, since the sample transporting apparatus 4 has the same functions as those of the sample transporting apparatus 3, the descriptions of such differences in components are omitted.

By means of the rack overtaking transporter 421, the sample transporting apparatus 4 receives a sample rack L transported from the adjacent upstream sample transporting apparatus 3. Then, the sample transporting apparatus 4 moves the sample rack L to the unprocessed rack holder 43 and sends out the sample rack L from the unprocessed rack holder 43 to the rack transporter 45, by means of a rack send-out part which is not shown. The sample transporting apparatus 4 further transports the sample rack L by means of the rack transporter 45 to the smear preparing apparatus 6, thereby supplying samples to the smear preparing apparatus 6. A sample rack L that accommodates sample containers for which sample aspiration has been completed is transported by the rack transporter 45 and sent out to the processed rack holder 44 by a rack send-out part which is not shown. A sample rack L held by the processed rack holder 44 is moved to the rack returning transporter 431 and transported by the rack returning transporter 431 to the sample transporting apparatus 3 disposed adjacent to, i.e., preceding, the sample transporting apparatus 4 (i.e., disposed upstream in the transporting direction from the sample transporting apparatus 4).

<Configuration of Blood Cell Analyzer 5>

The blood cell analyzer 5 is a blood cell analyzer for multi test items that uses optical flow cytometry. The blood cell analyzer 5 obtains side scattered light intensity, fluorescence intensity, and the like regarding blood cells contained in a blood sample. Based on such obtained information, the blood cell analyzer 5 classifies the blood cells in the sample into their respective types, and counts blood cells of each type. The blood cell analyzer 5 creates and displays a scattergram in which the blood cells are classified by color based on their respective types. The blood cell analyzer 5 includes the measurement units 51, 52, 53, and the information processing unit 54. The measurement units 51, 52, and 53 measure blood samples. The information processing unit 54 processes measurement data outputted from the measurement units 51, 52, and 53 and displays analysis results of the blood samples that are obtained from the measurement data processing.

As shown in FIG. 1, the blood cell analyzer 5 includes the three measurement units 51, 52, and 53 and the one information processing unit 54. The information processing unit 54 is communicably connected to the three measurement units 51, 52, and 53 so that the information processing unit 54 can control the operations of the measurement units 51, 52, and 53. The information processing unit 54 is also communicably connected to the three sample transporting apparatuses 3 which are arranged at the front of the three measurement units 51, 52, and 53, respectively.

Figure 7:
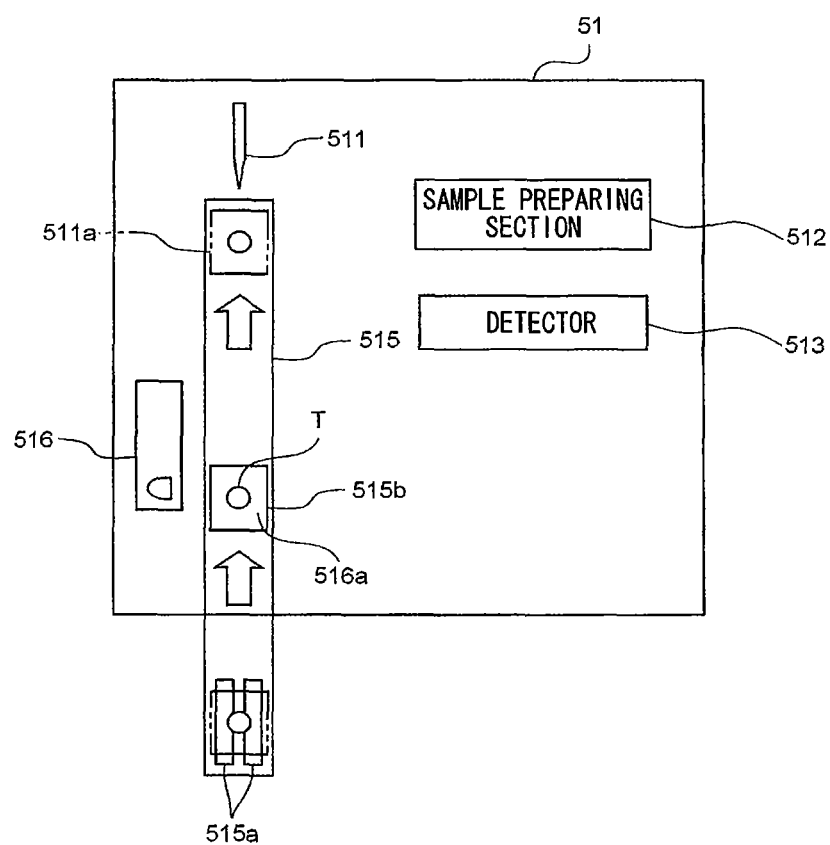
FIG. 7 is a block diagram showing a configuration of a measurement unit included in the blood analyzer according to the first embodiment.

FIG. 7 is a block diagram showing a configuration of the measurement unit 51. As shown in FIG. 7, the measurement unit 51 includes: a sample aspirator 511 for aspirating a blood sample from a sample container (blood collection tube) T; a sample preparing section 512 for preparing, from the blood aspirated by the sample aspirator 511, a measurement sample to be used in measurement; and a detector 513 for detecting blood cells from the measurement sample prepared by the sample preparing section 512. Further, the measurement unit 51 includes: a loading opening (not shown) through which a sample container T accommodated in a sample rack L transported by the rack transporter 35 of the corresponding sample transporting apparatus 3 is loaded into the measurement unit 51; and a sample container transporter 515 for loading a sample container T from a sample rack L into the measurement unit 51 and transporting the sample container T to an aspirating position at which the sample aspirator 511 aspirates a sample from the sample container T.

The sample aspirator 511 has an aspiration tube (not shown) at its tip. The sample aspirator 511 is movable in vertical directions. When the sample aspirator 511 is moved downward, the aspiration tube penetrates the cap CP of the sample container T that has been transported to the aspirating position, and aspirates the blood in the sample container T.

The sample preparing section 512 includes multiple reaction chambers (not shown). The sample preparing section 512 is connected to reagent containers that are not shown, and is configured to supply the reaction chambers with respective reagents such as a stain reagent, a hemolytic agent, and a diluent. The sample preparing section 512 is also connected to the aspiration tube of the sample aspirator 511. Accordingly, the sample preparing section 512 is configured to supply the reaction chambers with a blood sample aspirated by the aspiration tube. The sample preparing section 512 mixes and stirs the sample with a reagent in each reaction chamber, thereby preparing samples for measurement performed by the detector 513 (measurement samples).

The detector 513 is configured to perform RBC (red blood cells) detection and PLT (platelets) detection by a sheath flow DC detection method. In the RBC and PLT detections by the sheath flow DC detection method, a measurement sample prepared by mixing the sample with the diluent is measured, and data obtained from the measurement is analyzed by the information processing unit 54. In this manner, RBC and PLT are measured. Further, the detector 513 is configured to perform HGB (hemoglobin) detection by an SLS-hemoglobin method and WBC (white blood cells) detection by flow cytometry using a semiconductor laser. The detector 513 performs measurement on a measurement sample that is prepared by mixing the sample with the hemolytic agent and the diluent, and data obtained from the measurement is analyzed by the information processing unit 54. In this manner, WBC measurement is performed. RBC, PLT, HGB, and WBC are measured when a measurement item CBC (complete blood count) is selected.

The sample container transporter 515 includes a hand part 515a configured to hold a sample container T. The hand part 515a includes a pair of gripping members which are arranged so as to face each other. The hand part 515a is configured to move the gripping members alternately toward and away from each other. The hand part 515a holds the sample container T by moving the gripping members toward each other when a sample container T is located between the gripping members. The sample container transporter 515 is configured to move the hand part 515a in the vertical directions and in the front-rear directions (Y directions). The sample container transporter 515 is also configured to rock the hand part 515a. The sample container transporter 515 holds, by means of the hand part 515a, a sample container T that is accommodated in a sample rack L and that is located at a sample supply position. Then, the sample container transporter 515 moves the hand part 515a holding the sample container T upward to remove the sample container T from the sample rack L, and rocks the hand part 515a. In this manner, the sample in the sample container T can be agitated.

The sample container transporter 515 further includes a sample container setting part 515b which has a hole through which a sample container T can be inserted. A sample container T held by the hand part 515a in the above manner is moved after the agitating operation is completed, so as to be inserted through the hole of the sample container setting part 515b. Thereafter, the gripping members are moved away from each other, and the sample container T is set in the sample container setting part 515b, accordingly. The sample container setting part 515b is horizontally movable in the Y directions, based on the dynamics of a stepping motor which is not shown. Within the measurement unit 51, a bar code reader 516 is provided. The sample container setting part 515b is movable to a bar code reading position 516a near the bar code reader 516 and to an aspirating position 511a at which the sample aspirator 511 performs an aspirating operation. When the sample container setting part 515b has moved to the bar code reading position 516a, the sample container T set in the sample container setting part 515b is horizontally rotated by a rotation mechanism which is not shown, and the bar code reader 516 reads the sample bar code of the sample container T during the rotation. In this manner, even if the bar code label BL1 of the sample container T is located on the side opposite to the bar code reader 516, the bar code label BL1 can be caused to face the bar code reader 516 by rotating the sample container T. Accordingly, the bar code reader 516 can read the sample bar code. When the sample container setting part 515b has moved to the aspirating position 511a, the sample aspirator 511 aspirates the sample from the sample container T set in the sample container setting part 515b.

The measurement units 52 and 53 both have the same configuration as that of the measurement unit 51, and include a sample aspirator, a sample preparing section, a detector, and a sample container transporter. However, the detector of the measurement unit 52 is different from the detector 513 of the measurement unit 51 in that the detector of the measurement unit 52 is configured to perform not only CBC but also classification of white blood cells into five types (i.e., a measurement item DIFF). To be more specific, the detector of the measurement unit 52 is configured to perform the detection of WBC (white blood cells), NEUT (neutrophils), LYMPH (lymphocytes), EO (eosinophils), BASO (basophils), and MONO (monocytes) by flow cytometry using a semiconductor laser. The detector of the measurement unit 52 performs measurement on a measurement sample that is prepared by mixing a sample with a stain reagent, a hemolytic agent, and a diluent. Then, the information processing unit 54 analyzes data obtained from the measurement. In this manner, NEUT, LYMPH, EO, BASO, MONO, and WBC are measured.

The detector of the measurement unit 53 is different from the detectors of the measurement units 51 and 52 in that the detector of the measurement unit 53 is configured to measure reticulocytes (RET) in addition to performing CBC and DIFF. RET measurement is performed in the following manner: a measurement sample is prepared by mixing a sample with a reagent used for RET measurement, and the measurement sample is supplied to an optical detector of the detector, which optical detector is used for WBC/DIFF detection (classification of white blood cells into five types).

Figure 8:
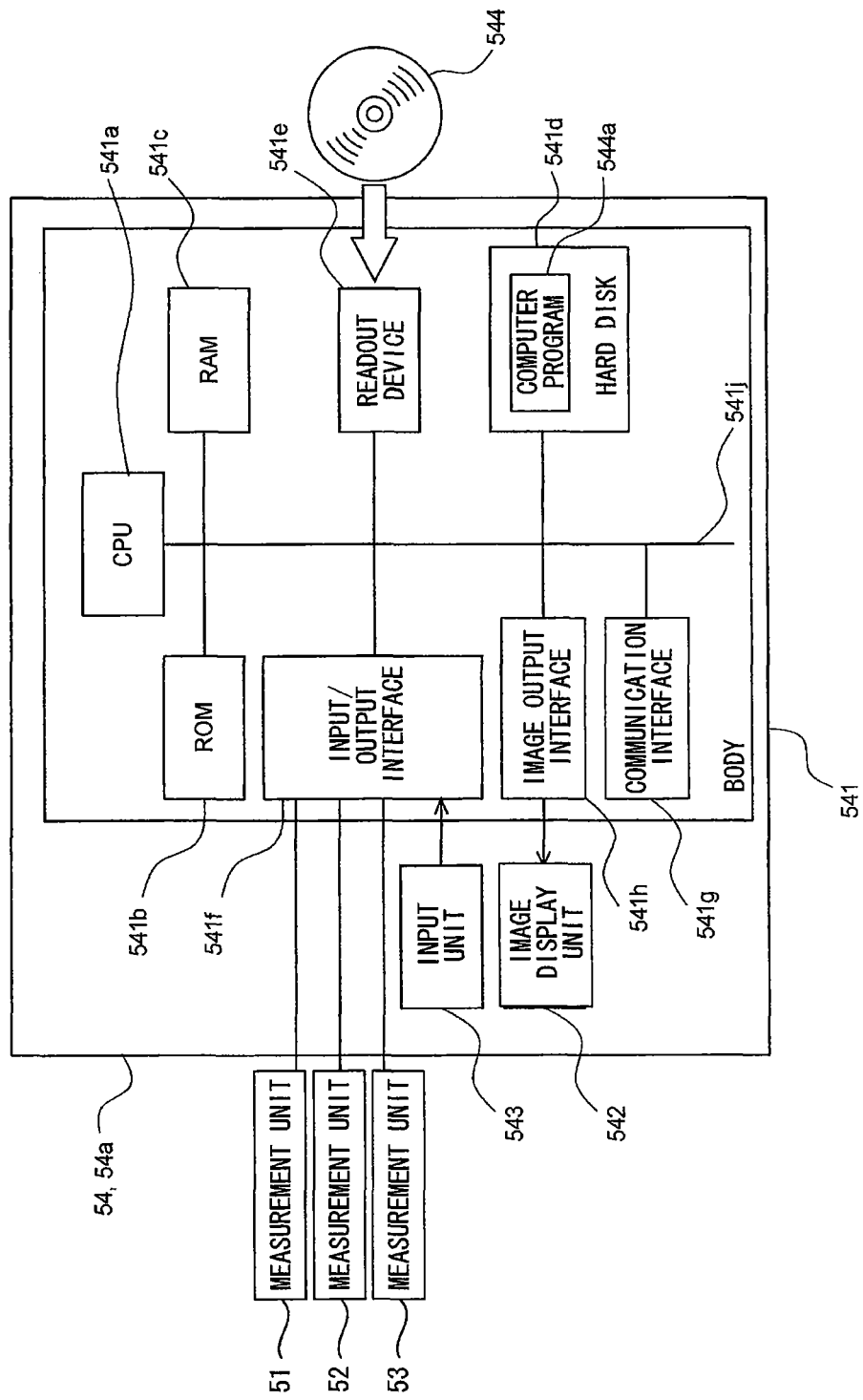
FIG. 8 is a block diagram showing a configuration of an information processing unit included in the blood analyzer according to the first embodiment.

Next, a configuration of the information processing unit 54 is described. The information processing unit 54 is structured as a computer. FIG. 8 is a block diagram showing a configuration of the information processing unit 54. The information processing unit 54 is realized by a computer 54a. As shown in FIG. 8, the computer 54a includes a body 541, an image display unit 542, and an input unit 543. The body 541 houses a CPU 541a, a ROM 541b, a RAM 541c, a hard disk 541d, a readout device 541e, an input/output interface 541f, a communication interface 541g, and an image output interface 541h. The CPU 541a, ROM 541b, RAM 541c, hard disk 541d, readout device 541e, input/output interface 541f, communication interface 541g, and the image output interface 541h are connected to one another via a bus 541j.

The readout device 541e is configured to read from a portable storage medium 544 a computer program 544a for causing a computer to act as the information processing unit 54, and install the computer program 544a in the hard disk 541d.

<Configuration of Smear Preparing Apparatus 6>

The smear preparing apparatus 6 prepares a smear in the following manner: aspirate a blood sample; drop the blood sample on a glass slide; thinly spread and dry the blood sample on the glass slide; and supply a stain solution to the glass slide, thereby staining the blood on the glass slide.

Figure 9:
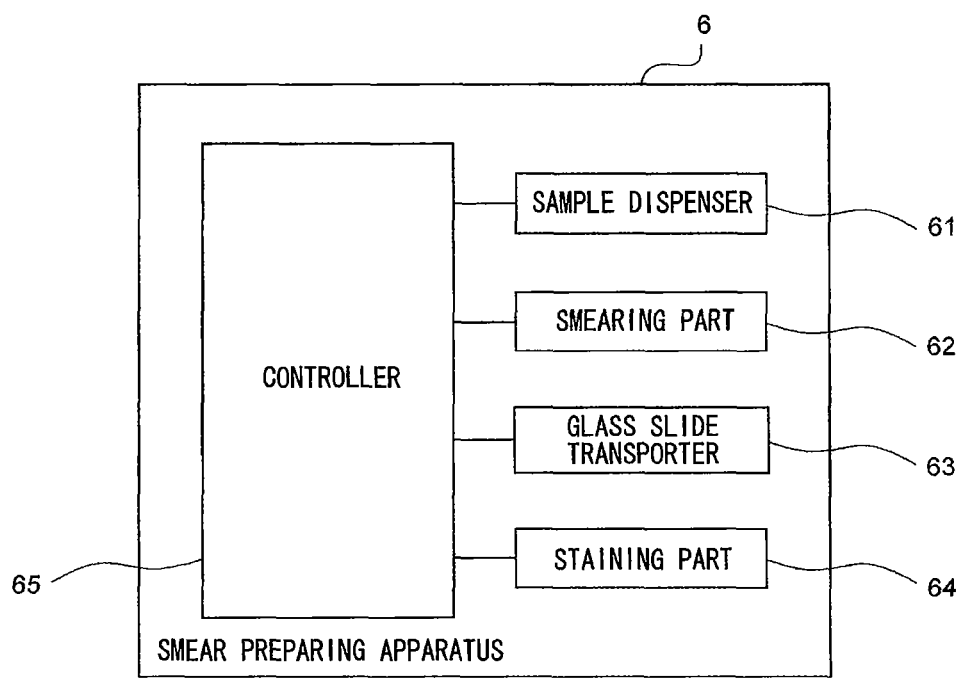
FIG. 9 is a block diagram showing a schematic configuration of the smear preparing apparatus according to the first embodiment.

FIG. 9 is a block diagram showing a schematic configuration of the smear preparing apparatus 6. As shown in FIG. 9, the smear preparing apparatus 6 includes a sample dispenser 61, a smearing part 62, a glass slide transporter 63, a staining part 64, and a controller 65.

The sample dispenser 61 includes an aspiration tube (not shown). The sample dispenser 61 pierces, with the aspiration tube, the cap CP of a sample container T held by a sample rack L that has been transported on the rack transporter 45 of the sample transporting apparatus 4, and then aspirates a blood sample from the sample container T. Also, the sample dispenser 61 is configured to drop the aspirated blood sample onto a glass slide. The smearing part 62 is configured to smear the glass slide with the blood sample dropped thereon, dry the blood sample, and perform printing on the glass slide.

The glass slide transporter 63 is provided for causing the glass slide, on which the blood sample has been smeared by the smearing part 62, to be accommodated in a cassette which is not shown, and for transporting the cassette. The staining part 64 supplies a stain solution to the glass slide accommodated in the cassette that has been transported by the glass slide transporter 63 to a staining position. The controller 65 controls the sample dispenser 61, the smearing part 62, the glass slide transporter 63, and the staining part 64 in accordance with a smear preparation instruction provided from any sample transporting apparatus 3, thereby performing a smear preparing operation as described above.

<Configuration of System Control Apparatus 8>

The system control apparatus 8 is structured as a computer, and controls the entire sample processing apparatus 1. The system control apparatus 8 receives a rack number of a sample rack L from the sample feeding/collecting apparatus 2, and determines a transportation destination of the sample rack L.

Figure 10:
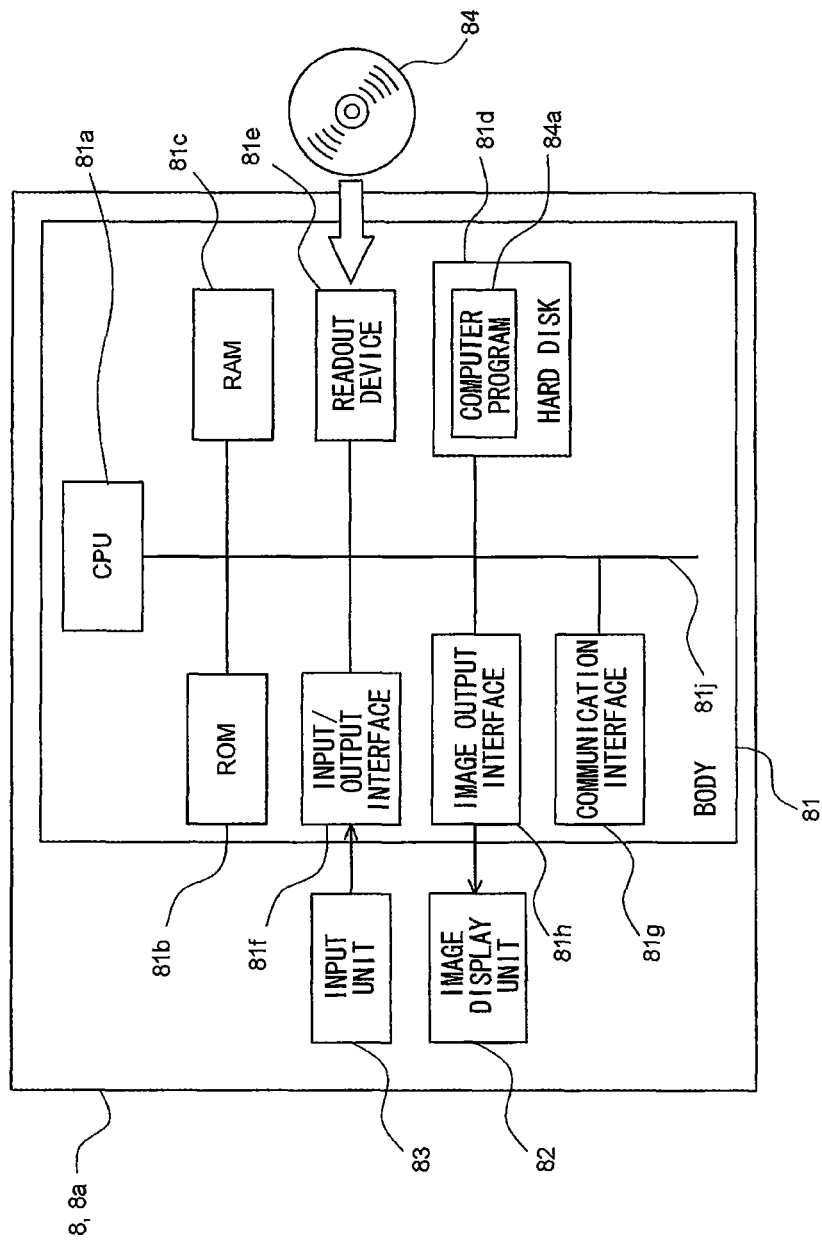
FIG. 10 is a block diagram showing a configuration of a system control apparatus according to the first embodiment.

FIG. 10 is a block diagram showing a configuration of the system control apparatus 8 according to the present embodiment. The system control apparatus 8 is realized by a computer 8a. As shown in FIG. 10, the computer 8a includes a body 81, an image display unit 82, and an input unit 83. The body 81 houses a CPU 81a, a ROM 81b, a RAM 81c, a hard disk 81d, a readout device 81e, an input/output interface 81f, a communication interface 81g, and an image output interface 81h. The CPU 81a, ROM 81b, RAM 81c, hard disk 81d, readout device 81e, input/output interface 81f, communication interface 81g, and the image output interface 81h are connected to one another via a bus 81j.

The readout device 81e is configured to read from a portable storage medium 84 a system control program 84a for causing a computer to act as the system control apparatus 8, and to install the system control program 84a in the hard disk 81d.

<Configuration of Laboratory Test Information Management Apparatus 9>

The laboratory test information management apparatus 9 is an apparatus for managing information about tests performed in a laboratory, that is, a so-called LIS (Laboratory Information System). The laboratory test information management apparatus 9 is connected not only to the blood cell analyzer 5 but also to other laboratory sample testing apparatuses. The laboratory test information management apparatus 9 receives a measurement order that has been inputted by an operator or transmitted from another apparatus such as an electronic medical chart system, and stores and manages the measurement order. Further, the laboratory test information management apparatus 9 receives an order request from the system control apparatus 8, and in response to the order request, transmits a measurement order to the system control apparatus 8. Also, the laboratory test information management apparatus 9 receives analysis results from the blood cell analyzer 5, and stores and manages the analysis results.

The laboratory test information management apparatus 9 is structured as a computer that includes a CPU, a ROM, a RAM, a hard disk, a communication interface, and the like. The communication interface is connected to the LAN mentioned above, and is configured to communicate with the system control apparatus 8 and the information processing unit 54 of the blood cell analyzer 5. The hard disk stores measurement orders. Each measurement order includes information such as sample IDs and measurement items for which measurement is to be performed. Upon receiving, from another apparatus, measurement order request data that contains sample IDs, the laboratory test information management apparatus 9 reads measurement orders corresponding to the sample IDs from the hard disk, and transmits the measurement orders to the apparatus that has transmitted the measurement order request data. Other than the above, the configuration of the laboratory test information management apparatus 9 is the same as that of the other computers described above, and therefore, a further description thereof is omitted.

[Operations of Sample Processing Apparatus]

Hereinafter, operations of the sample processing apparatus 1 according to the present embodiment will be described.

<Sample Transporting Operation of Sample Feeding/Collecting Apparatus 2>

Figure 11:
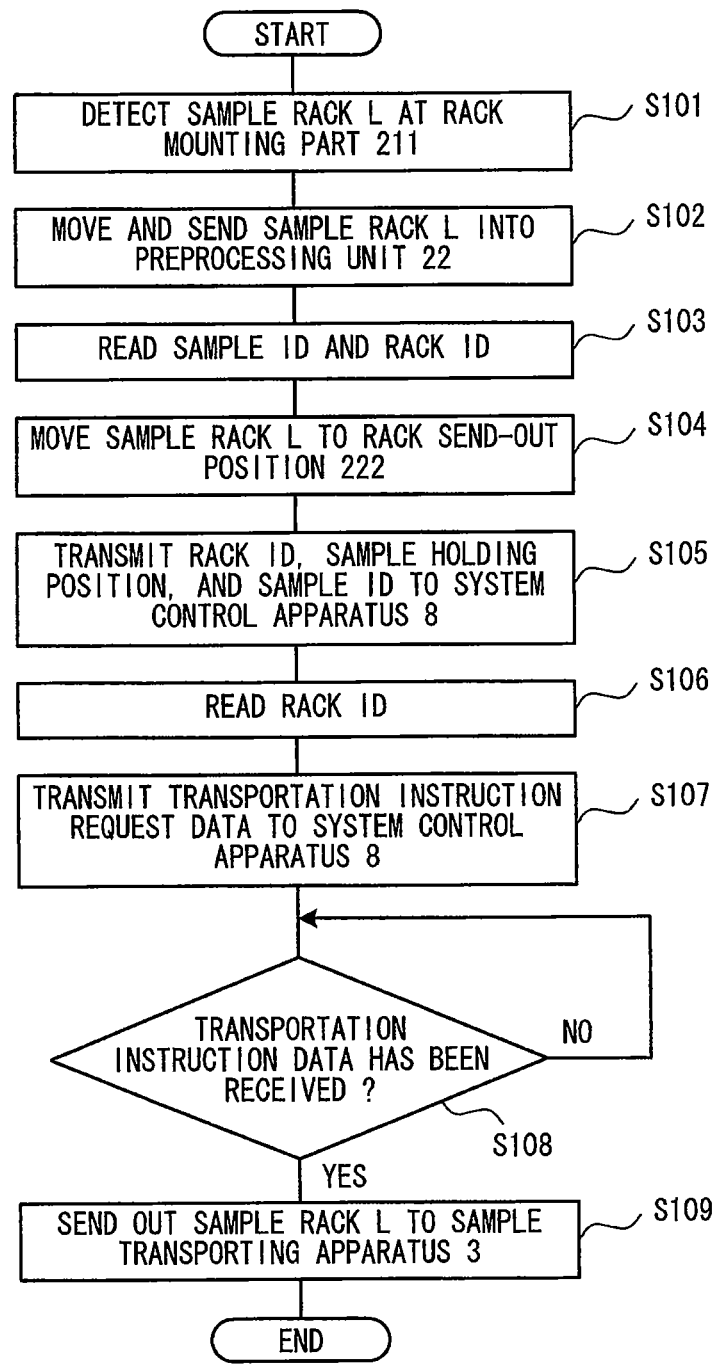
FIG. 11 is a flowchart showing a flow of a sample transporting operation performed by the sample feeding/collecting apparatus according to the first embodiment.

FIG. 11 is a flowchart showing a flow of a sample transporting operation performed by the sample feeding/collecting apparatus 2. In order to start sample processing by the sample processing apparatus 1, an operator operates the operation panel 21b of the sample feeding unit 21 to provide the sample processing apparatus 1 with an instruction to start sample processing. Thereafter, when a sample rack L has been fed into the sample feeding unit 21, the sensors 212 and 213 detect the sample rack L mounted in the rack mounting part 211 (step S101). A control program executed by the controller 21a of the sample feeding unit 21 is an event driven program. When an event occurs in which the sensors 212 and 213 detect the sample rack L, the controller 21a of the sample feeding unit 21 performs the process at step S102.

At step S102, the controller 21a drives the engagement portions 211a to move the sample rack L backward to the rack send-out position 214. Further, the controller 21a drives the protruding portion 215 to send out the sample rack L from the rack send-out position 214 to the preprocessing unit 22 (step S102).

The sample rack L sent out from the rack send-out position 214 of the sample feeding unit 21 to the left enters the preprocessing unit 22 and arrives at the bar code reading position. When the sample rack L arrives at the bar code reading position, the controller 22a of the preprocessing unit 22 controls the bar code reader 22b to read the sample ID of each sample container T held by the sample rack L and the rack ID of the sample rack L (step S103). When the sample rack L arrives at the bar code reading position, the optical sensor of the bar code reader 22b detects the presence of sample containers T, and the bar code reader 22b reads the sample bar code of each sample container T multiple times consecutively. When data of sample IDs read from the multiple readings is constant among the multiple readings, the sample bar code reading is determined to be successful. In this manner, sample IDs are read from sample bar codes of all the sample containers T held by the sample rack L. Here, sample holding positions on the sample rack L and the read sample IDs of the sample containers T held in the sample holding positions are associated with each other and stored in the controller 22a. In the detection of sample containers T by the optical sensor, if there is no single sample bar code having been read during a predetermined time period, or if data of a sample bar code that has been read multiple times during the predetermined time period is not constant among the multiple readings, or if a sample bar code has been read only once during the predetermined time period, then the sample bar code reading is determined to have failed. If the bar code reading has failed for a sample, the controller 22a of the preprocessing unit 22 stores, instead of the sample ID of the sample, information indicating an error in sample ID reading (sample bar code reading error information) in association with a sample holding position of the sample rack L, in which position the sample is being held.

Next, the controller 22a controls the engagement portions 221a to move the sample rack L forward within the rack mounting part 221 to the rack send-out position 222 (step S104). The controller 22a transmits the stored rack ID, sample holding positions, and sample IDs to the system control apparatus 8 (step S105). As described below, upon receiving the rack ID, the sample holding positions, and the sample IDs, the system control apparatus 8 requests measurement orders from the laboratory test information management apparatus 9, and stores the measurement orders in association with the rack ID, the sample holding positions, and the sample IDs.

When the sample rack L arrives at the rack send-out position 222, the controller 22a controls the bar code reader 222a to read the rack ID from the rack bar code of the sample rack L (step S106), and transmits to the system control apparatus 8 transportation instruction request data that contains the read rack ID (step S107). Upon receiving the transportation instruction request data, the system control apparatus 8 retrieves from the hard disk measurement orders that are associated with the rack ID. Based on the measurement orders, the system control apparatus 8 determines a transportation destination of the sample rack L, and transmits to the preprocessing unit 22 transportation instruction data for transporting the sample rack L to the determined transportation destination. The controller 22a stands by to receive the transportation instruction data from the system control apparatus 8 (NO at step S108). Upon receiving the transportation instruction data (YES at step S108), the controller 22a controls the protruding portion 225 to send out the sample rack L to the left from the rack send-out position 222 (step S109). Then, the controller 22a ends the processing.

Each time a sample rack L is newly fed into the sample feeding unit 21, the above-described process from step S101 to step S109 is performed.

<Measurement Order Obtaining Operation of System Control Apparatus 8>

Figure 12:
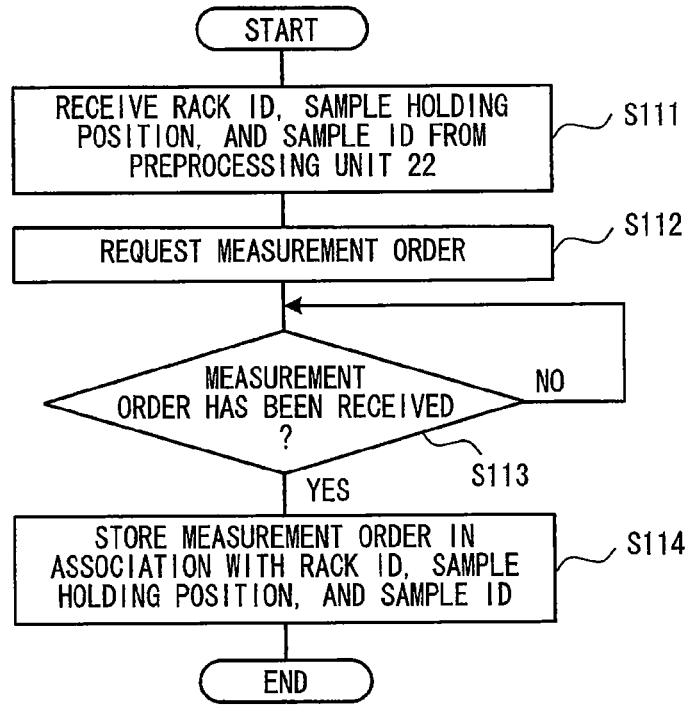
FIG. 12 is a flowchart showing a flow of a measurement order obtaining operation performed by the system control apparatus according to the first embodiment.

FIG. 12 is a flowchart showing a flow of a measurement order obtaining operation performed by the system control apparatus 8. The rack ID, the sample holding positions, and the sample IDs which have been transmitted from the preprocessing unit 22 are received by the communication interface 81g of the system control apparatus 8 (step S111). The system control program 84a is an event driven program. When an event of receiving the rack ID, the sample holding positions, and the sample IDs occurs, the CPU 81a performs the process at step S112.

At step S112, the CPU 81a requests a measurement order from the laboratory test information management apparatus 9 for each sample ID received by the communication interface 81g, by transmitting to the laboratory test information management apparatus 9 measurement order request data that contains the sample IDs (step S112). Next, the CPU 81a stands by to receive measurement orders for the samples of the sample rack L (NO at step S113). Upon receiving measurement orders (YES at step S113), the CPU 81a stores the measurement orders in the hard disk 81d in association with the rack ID, the sample holding positions, and the sample IDs (step S114). Then, the CPU81a ends the processing. Here, when the communication interface 81g receives, at step S111, data in which sample bar code reading error information instead of a sample ID is associated with a sample holding position, the CPU81a stores, instead of a sample ID, the sample bar code reading error information in association with the sample holding position.

<First Transportation Instruction Operation of System Control Apparatus 8>

Figure 13:
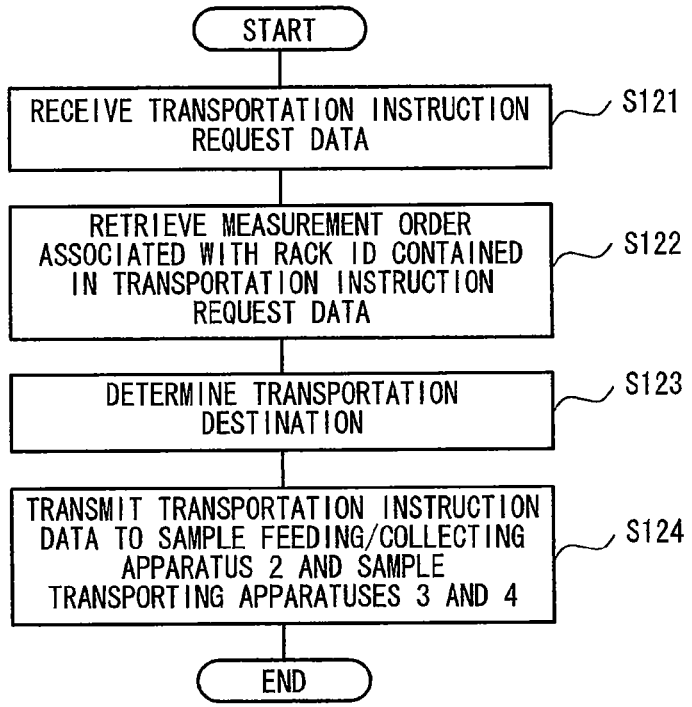
FIG. 13 is a flowchart showing a flow of a first transportation instruction operation performed by the system control apparatus according to the first embodiment.

FIG. 13 is a flowchart showing a flow of a first transportation instruction operation performed by the system control apparatus 8. The transportation instruction request data (the rack ID) read by the bar code reader 222a and transmitted from the preprocessing unit 22 is received by the communication interface 81g of the system control apparatus 8 (step S121). When an event occurs in which the rack ID is received by the communication interface 81, the CPU 81a performs the process at step S122.

At step S122, the CPU 81a retrieves from measurement orders stored in the hard disk 81d measurement orders associated with the rack ID received at step S121 (step S122). The CPU 81a manages the transportation status of the sample rack L in real time. This allows the CPU81a to determine which one, among the measurement units 51, 52, 53, and smear preparing apparatus 6, should be supplied with samples in order to realize the most efficient sample processing. When the measurement orders associated with the rack ID are retrieved, the CPU 81a specifies one among the measurement units 51, 52, 53, and smear preparing apparatus 6, which can perform sample processing most efficiently for processing items (the processing items may include measurement items and smear preparation) that are contained in the measurement orders. Then, the CPU 81a designates the specified unit or apparatus to be a transportation destination (step S123) of the rack.

Next, the CPU 81a transmits, to the sample feeding/collecting apparatus 2 and the sample transporting apparatuses 3 and 4, transportation instruction data which instructs the apparatuses to transport, by the overtaking line(s), the sample rack L to the sample transporting apparatus 3 or 4 corresponding to the designated transportation destination, which is one among the measurement units 51, 52, 53, and smear preparing apparatus 6 (step S124). Then, the CPU 81a ends the processing. The transportation instruction data contains the rack ID of the sample rack L as well as a sample holding position, a sample ID, and a measurement order for each sample held by the sample rack L. Here, the transportation instruction data does not contain a measurement order for a sample for which the sample bar code reading by the bar code reader 22b has failed. In the transportation instruction data, the sample holding position of the sample for which the sample bar code reading by the bar code reader 22b has failed is associated not with the sample ID of the sample but with sample bar code reading error information.

<First Transporting Operation of Sample Transporting Apparatus 3>

Figure 14:
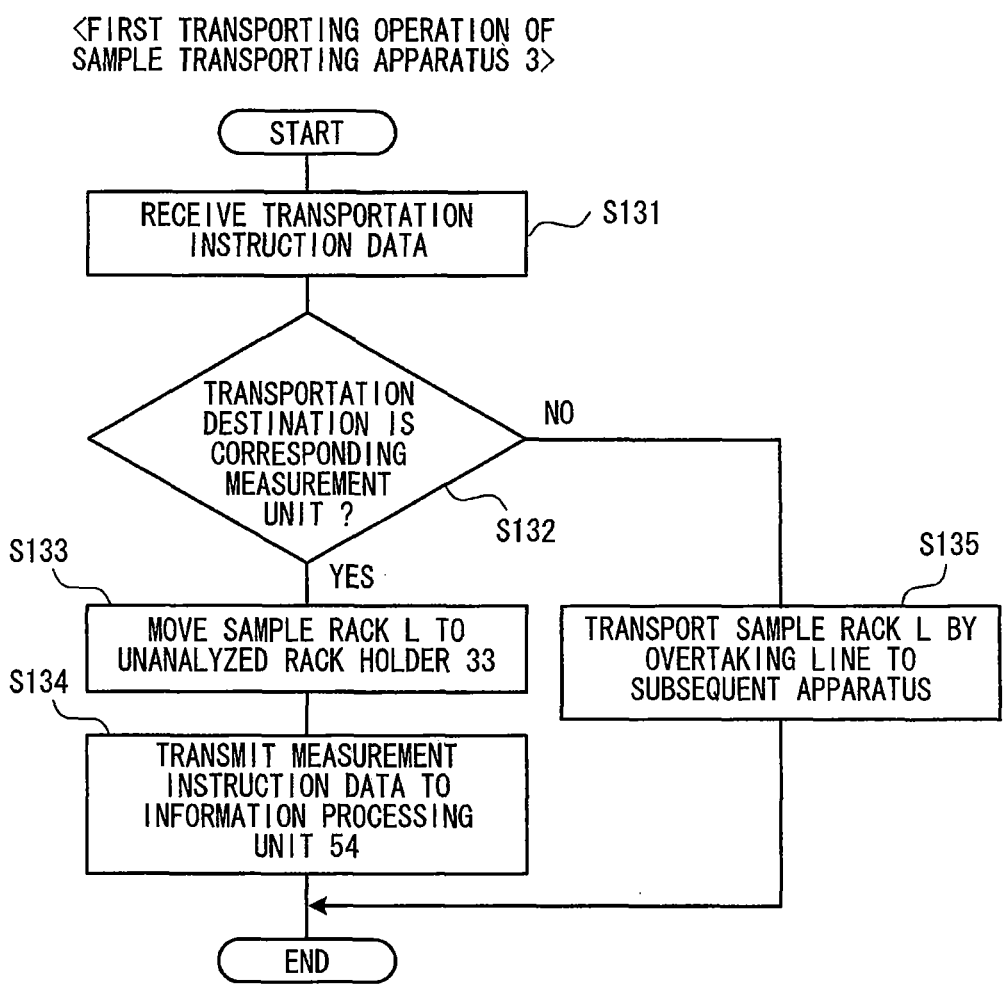
FIG. 14 is a flowchart showing a flow of a first transporting operation performed by each sample transporting apparatus used for the blood analyzer according to the first embodiment.

FIG. 14 is a flowchart showing a flow of a first transporting operation performed by each sample transporting apparatus 3. When the preprocessing unit 22 receives the transportation instruction data, the controller 22a causes the protruding portion 225 to move to the left, thereby transporting a sample rack L located at the rack send-out position 222 onto the rack overtaking transporter 321 of the sample transporting apparatus 3 that is disposed most upstream in the transporting direction among the sample transporting apparatuses 3. When the sample transporting apparatuses 3 receive the transportation instruction data (step S131), each controller 32 of the sample transporting apparatuses 3 performs the process at step S132.

At step S132, based on the transportation instruction data, the controller 32 of each sample transporting apparatus 3 determines whether or not the transportation destination of the sample rack L is the corresponding one of the measurement units 51, 52, and 53 (step S132). To be specific, the controller 32 of the sample transporting apparatus 3 that is disposed most upstream in the transporting direction among the sample transporting apparatuses determines whether or not the transportation destination is the measurement unit 51. Likewise, the controller 32 of the sample transporting apparatus 3 that is the second sample transporting apparatus 3 when counted from the sample transporting apparatus 3 that is disposed most upstream in the transporting direction determines whether or not the transportation destination is the measurement unit 52. When, among the controllers 32, a controller 32 determines the transportation destination to be a measurement unit that corresponds to the sample transporting apparatus 3 of which the controller 32 is a part (YES at step S132), the controller 32 drives the transporting mechanism 31 to transport, by means of the rack overtaking transporter 321, the sample rack L into that sample transporting apparatus 3. The controller 32 causes the rack send-out part 322 to move backward, thereby moving the sample rack L, which is located at the unanalyzed rack send-out position 323, to the unanalyzed rack holder 33 (step S133). The controller 32 transmits measurement instruction data to the information processing unit 54 (step S134). The measurement instruction data contains the rack ID of the sample rack L and a sample holding position and a sample ID for each sample held by the sample rack L (but contains sample bar code reading error information, instead of a sample ID, for a sample for which the sample ID reading by the bar code reader 22b has failed), and contains a measurement order for each sample held by the sample rack L (but does not contain a measurement order for a sample for which the sample ID reading by the bar code reader 22b has failed). Then, the controller 32 ends the processing.

On the other hand, at step S132, if a controller 32 among the controllers 32 determines that the transportation destination is not a measurement unit that corresponds to the sample transporting apparatus 3 of which the controller 32 is a part (NO at step S132), then the controller 32 drives the transporting mechanism 31 to transport, by means of the rack overtaking transporter 321, the sample rack L into that sample transporting apparatus 3, and further transport the sample rack L from the sample transporting apparatus 3 to the subsequently positioned sample transporting apparatus 3 or 4 (step S135). Then, the controller 32 ends the processing.

<Rack Transporting Operation of Sample Transporting Apparatus 4>

Figure 15:
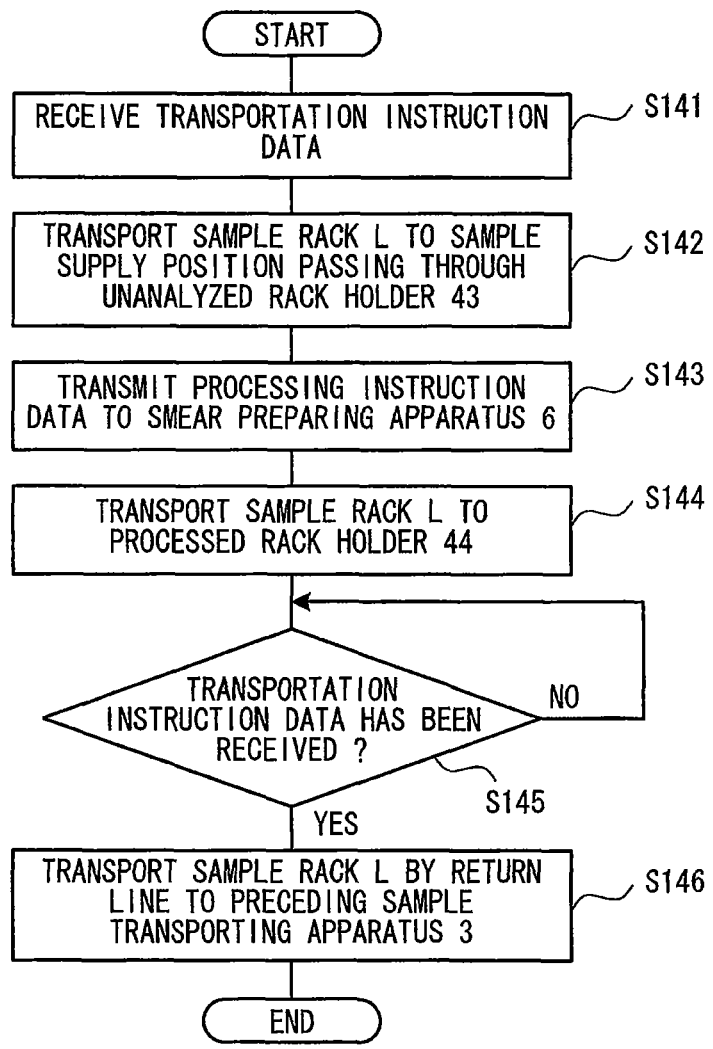
FIG. 15 is a flowchart showing a flow of a rack transporting operation performed by the sample transporting apparatus used for the smear preparing apparatus according to the first embodiment.

FIG. 15 is a flowchart showing a flow of a rack transporting operation performed by the sample transporting apparatus 4. When samples held by a sample rack L include a sample for which smear preparation is necessary, the rack overtaking transporter 321 of the sample transporting apparatus 3 that is disposed most downstream in the transporting direction among the sample transporting apparatuses 3 transports the sample rack L to the sample transporting apparatus 4. In this case, when the sample transporting apparatus 4 receives transportation instruction data (step S141), the controller 42 performs the process at step S142.

At step S142, the controller 42 drives the transport mechanism 41 to transport, by means of the rack overtaking transporter 421, the sample rack L into the sample transporting apparatus 4, and to move the sample rack L to the rack transporter 45, passing through the unprocessed rack holder 43 along the way. Further, the controller 42 drives the rack transporter 45 such that a sample container T of the sample rack L that contains a sample for which a smear is to be prepared is transported to a sample supply position (step S142). Next, the controller 42 transmits processing instruction data to the smear preparing apparatus 6 (step S143). The processing instruction data contains the rack ID of the sample rack L and a sample holding position and a sample ID for each sample held by the sample rack L (but contains sample bar code reading error information, instead of a sample ID, for a sample for which the sample ID reading by the bar code reader 22b has failed), and contains a measurement order for each sample held by the sample rack L (but does not contain a measurement order for a sample for which the sample ID reading by the bar code reader 22b has failed).

The smear preparing apparatus 6 aspirates, by means of the sample dispenser 61, the sample from the sample container T that has been transported to the sample supply position, and prepares a smear from the sample. Among the samples held by the sample rack L, such smear preparation is performed for all the samples that require smear preparation. After all the samples that require smear preparation are supplied to the smear preparing apparatus 6, the controller 42 performs control so as to transport the sample rack L to the processed rack holder 44 (step S144). When the smear preparation for the samples has been completed, the controller 65 of the smear preparing apparatus 6 transmits, to the system control apparatus 8 and the laboratory test information management apparatus 9, processing completion notification data that indicates the completion of the smear preparation. As described below, upon receiving the processing completion notification data, the system control apparatus 8 determines one among the sample feeding unit 21 and sample collection units 23, 24, and 25 to be a transportation destination of the sample rack L. Then, the system control apparatus 8 transmits, to the sample feeding/collecting apparatus 2, the sample transporting apparatuses 3, and the sample transporting apparatus 4, transportation instruction data which instructs the apparatuses to transport the sample rack L to the determined transportation destination. The controller 42 of the sample transporting apparatus 4 stands by to receive the transportation instruction data (NO at step S145). Upon receiving the transportation instruction data (YES at step S145), the controller 42 controls the transport mechanism 41 to move the sample rack L held by the processed rack holder 44 to the rack returning transporter 431 and transport, by means of the rack returning transporter 431, the sample rack L to the sample transporting apparatus 3 disposed preceding the sample transporting apparatus 4 (step S146). Then, the controller 42 ends the processing.

<Rack Transportation Control Operation of Blood Cell Analyzer 5>

Figure 16:
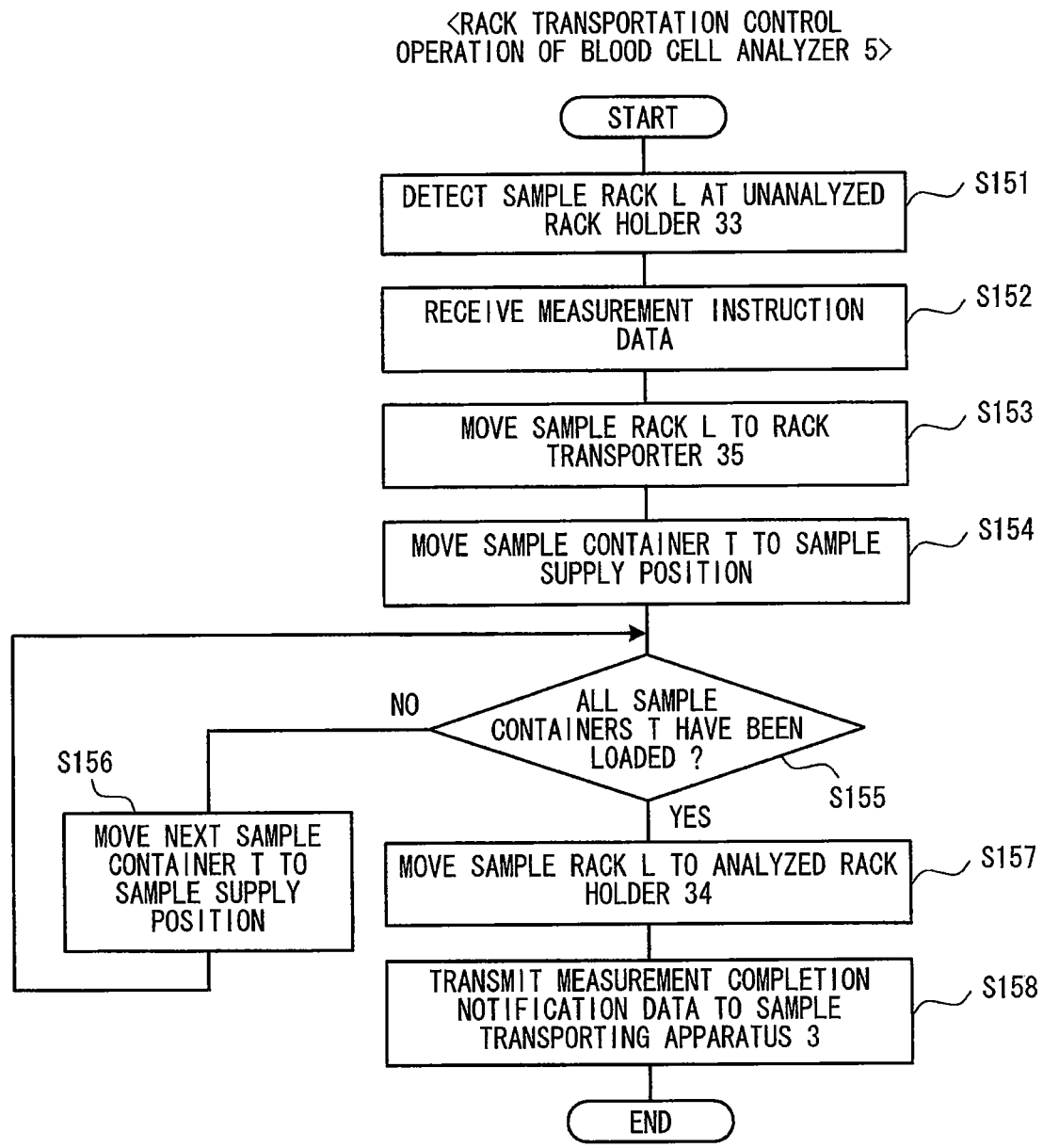
FIG. 16 is a flowchart showing a flow of a rack transportation control operation performed by the blood analyzer according to the first embodiment.

FIG. 16 is a flowchart showing a flow of a rack transportation control operation performed by the blood cell analyzer 5. The CPU 541a of the information processing unit 54 of the blood cell analyzer 5 performs the process at step S153 when a rack sensor provided in a sample transporting apparatus 3 among the sample transporting apparatuses 3 detects a sample rack L held by the unanalyzed rack holder 33 (step S151) and an event of receiving measurement instruction data from the sample transporting apparatus 3 occurs (step S152).

At step S153, the CPU 541a causes the rack send-in part 33b of the sample processing apparatus 3 to move backward, thereby moving the sample rack L to the rack transporter 35.

Next, the CPU 541a drives the rack transporter 35 to transport the sample rack L such that a sample container T held by the sample rack L is located at the sample supply position (step S154).

In a sample analysis operation described below, the sample container T located at the sample supply position is removed from the sample rack L and loaded into the corresponding measurement unit in which the sample is aspirated from the sample container T and analyzed. When the sample aspiration by the measurement unit is completed, the sample container T is returned to the sample rack L. Then, the CPU 541a determines whether or not all the sample containers T held by the sample rack L have been loaded into the measurement unit (step S155). If there is a sample container T that has not been loaded (NO at step S155), the CPU 541a drives the rack transporter 35 to transport the sample rack L such that a sample holding position in which a sample container T is detected next is located at the sample supply position (step S156). Then, the CPU 541a returns the processing to step S155.

When it is determined at step S155 that all the sample containers T held by the sample rack L have been loaded into the measurement unit (YES at step S155), the CPU 541a drives the rack transporter 35 to transport the sample rack L to the analyzed rack send-out position 391. Further, the CPU 541a drives the rack send-out part 39 to move the sample rack L from the analyzed rack send-out position 391 to the analyzed rack holder 34 (step S157). Then, the CPU 541a transmits measurement completion notification data that contains the rack ID of the sample rack L to the sample transporting apparatus 3 (step S158). Then, the CPU 541a ends the processing.

<Sample Analysis Operation of Blood Cell Analyzer 5>

Figure 17:
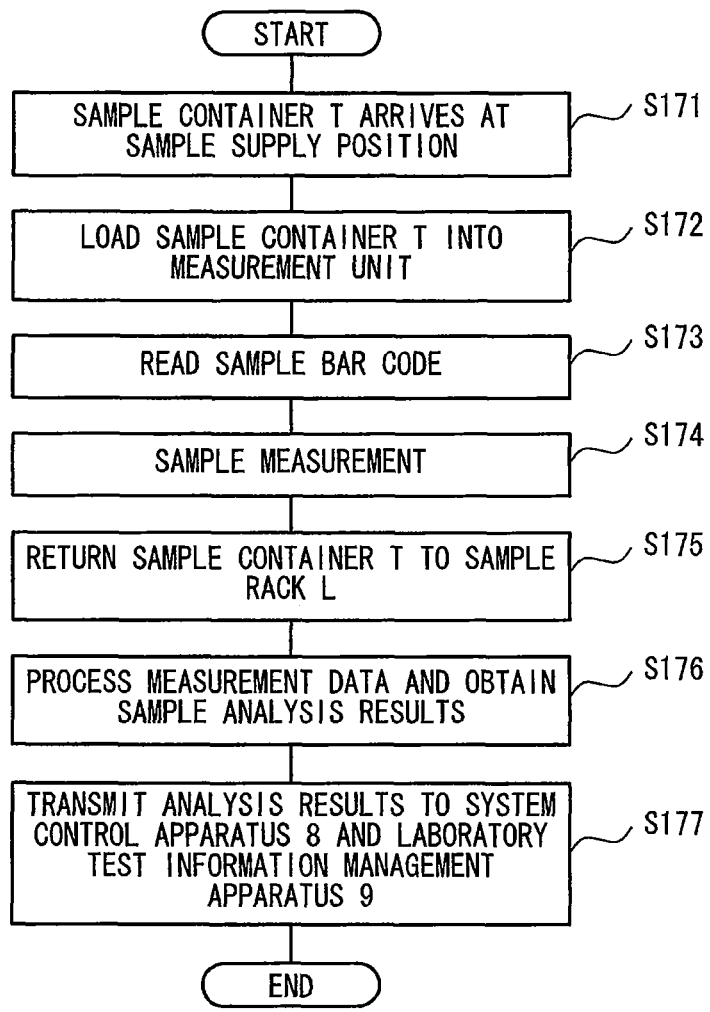
FIG. 17 is a flowchart showing a flow of a sample analysis operation performed by the blood analyzer according to the first embodiment.

FIG. 17 is a flowchart showing a flow of the sample analysis operation performed by the blood cell analyzer 5. Note that the above-described rack transportation control operation of the blood cell analyzer 5 and the sample analysis operation described here are performed in parallel by multitasking. When an event occurs in which a sample container T held by a sample rack L arrives at the sample supply position of a sample transporting apparatus 3 (step S171), the CPU 541a performs the process at step S172.

At step S172, the CPU 541a controls the sample container transporter 515 of the measurement unit that is disposed at the back of the sample transporting apparatus 3 which is transporting the sample rack L, so as to remove the sample container T located at the sample supply position from the sample rack L and load the sample container T into the measurement unit (step S172). Further, the CPU 541a controls the hand part 515a so as to rock the sample container T to agitate the sample therein. Thereafter, the CPU 541a controls the sample container transporter 515 so as to transport the sample container T to the bar code reading position 516a, and causes the bar code reader 516 to read the sample bar code of the sample container T, thereby obtaining the sample ID of the sample (step S173).

Subsequently, the CPU 541a performs measurement on the sample by using a corresponding measurement order contained in previously received measurement instruction data (step S174).

A necessary portion of the sample for the measurement is aspirated from the sample container T, and a measurement sample is prepared, and the measurement of the sample is started. The CPU 541a then controls the sample container transporter 515 of the measurement unit so as to return the sample container T from the measurement unit to the sample rack L (step S175). Thereafter, in the above-described rack transportation control operation, the rack transporter 35 is controlled such that the sample rack L is transported in the X1 direction.

Further, the CPU 541a processes measurement data obtained from the measurement of the sample, thereby obtaining analysis results of the sample (step S176).

In the process performed at S176, the presence or absence of an abnormality in the sample is determined, for example, by comparing numerical data obtained from the measurement with predetermined reference values. For example, when an RBC value is greater than a predetermined upper limit value, the CPU 541a determines that there is an abnormality in "increased red blood cells" in the sample, and stores, in the hard disk 541d, analysis results that include information indicating the abnormality (abnormality information). If an abnormal distribution of PLT particles is observed in a particle size distribution chart for PLT, the CPU 541a determines that there is an abnormality in the sample that is an "abnormality in a platelet particle size distribution", and stores, in the hard disk 541d, analysis results that include the abnormality information and that are associated with the rack ID and the sample holding position and the sample ID of the sample.

Such an abnormality in the sample may require retesting (re-measurement) of the sample. In the process performed at S176, in the case where an abnormality is detected in the sample as above, if the abnormality in the sample requires retesting, then the CPU 541a generates analysis results including information that indicates necessity of retesting and that indicates a measurement item for which the retesting is to be performed (hereinafter, referred to as retesting information), and stores the analysis results in the hard disk 541d in association with the rack ID and the sample holding position and the sample ID of the sample. The retesting is not limited to one performed by the sample processing apparatus 1 but includes one performed by an apparatus different from the sample processing apparatus 1 as well as a microscopic examination performed by a laboratory technician. In the case of performing a microscopic examination, it is necessary to prepare a smear from the sample by using the smear preparing apparatus 6.

The CPU 541a transmits the analysis results obtained in the above manner to the system control apparatus 8 and the laboratory test information management apparatus 9 (step S177), and then ends the processing.

<Second Transportation Instruction Operation of System Control Apparatus 8>

Figure 18A:
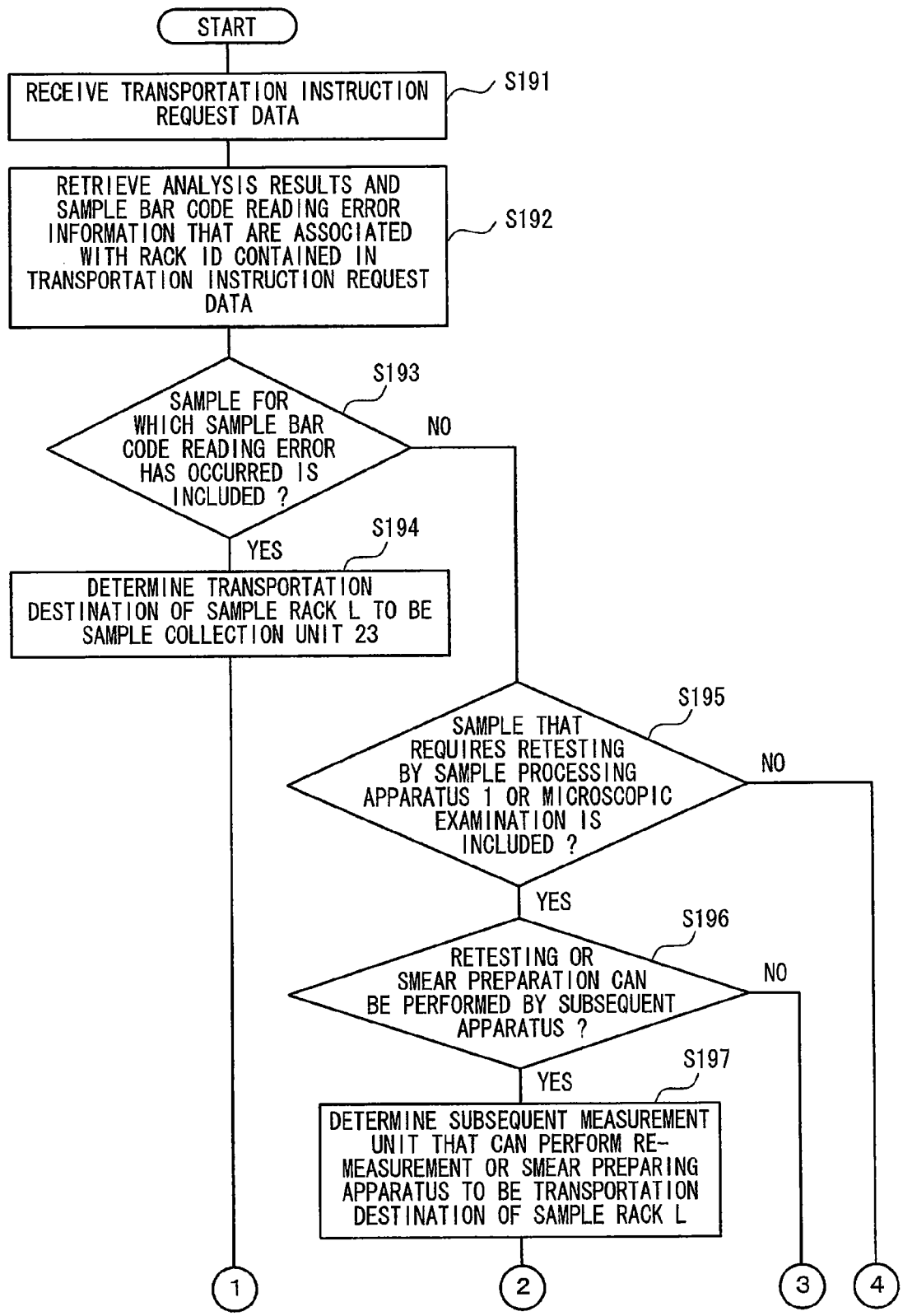
FIG. 18A is the first half of a flowchart showing a flow of a second transportation instruction operation performed by the system control apparatus according to the first embodiment.
Figure 18B:
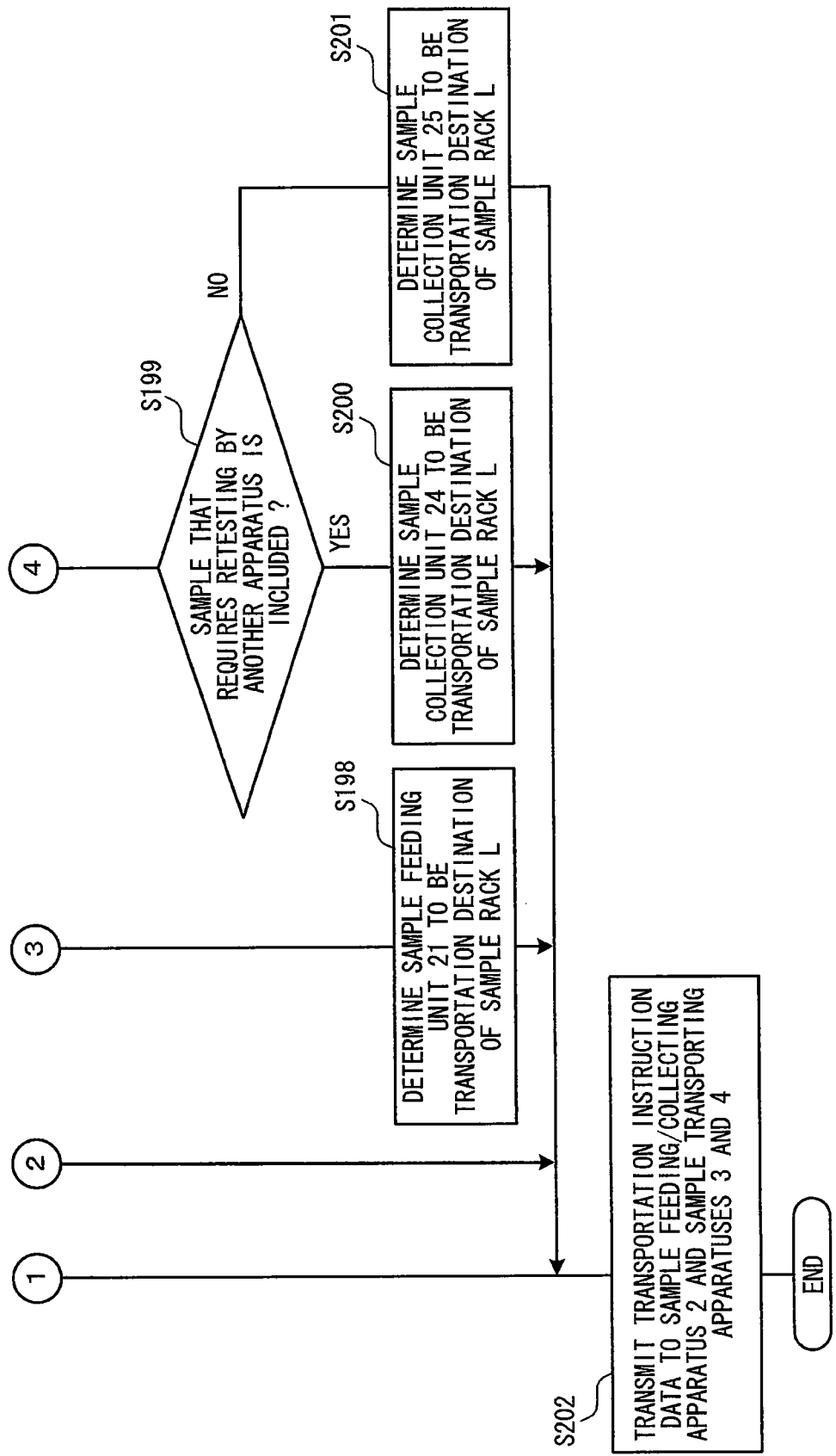
FIG. 18B is the second half of the flowchart showing the flow of the second transportation instruction operation performed by the system control apparatus according to the first embodiment.

FIG. 18A and FIG. 18B show a flowchart that illustrates a flow of a second transportation instruction operation performed by the system control apparatus 8. As described below, after the measurement of the samples is completed for the sample rack L, the sample rack L is moved from the analyzed rack send-out position 391 to the analyzed rack holder 34 of the sample transporting apparatus 3, and detected by the rack sensor provided in the sample transporting apparatus 3. Also, the measurement completion notification data transmitted from the information processing unit 54 is received by the sample transporting apparatus 3. In response, the sample transporting apparatus 3 transmits, to the system control apparatus 8, transportation instruction request data that contains the rack ID of the sample rack L. When an event occurs in which the system control apparatus 8 receives the transportation instruction request data (step S191), the CPU 81a of the system control apparatus 8 performs the process at step S192.

At step S192, the CPU 81a retrieves, from the hard disk 81d, analysis results and sample bar code reading error information that are associated with the rack ID contained in the received transportation instruction request data (i.e., analysis results and sample bar code reading error information about all the samples held by the sample rack L identified by the rack ID) (step S192). Next, the CPU 81a determines a transportation destination of the sample rack L. This process is described below in detail. The CPU 81a determines whether or not the samples held by the sample rack L include a sample that has not been measured (step S193). This determination is based on whether or not sample bar code reading error information associated with the rack ID is stored in the hard disk 81d, since measurement is not performed on a sample for which a sample bar code reading error has occurred. If the samples held by the sample rack L include a sample that has not been measured, that is, if sample bar code reading error information associated with the rack ID is stored in the hard disk 81*d* (YES at step S193), then the CPU 81*a* determines a transportation destination of the sample rack L to be the sample collection unit 23 (step S194).

If the samples held by the sample rack L do not include a sample that has not been measured, that is, if sample bar code reading error information associated with the rack ID is not stored in the hard disk 81*d* (NO at step S193), then the CPU 81*a* determines whether the samples held by the sample rack L include a sample that requires retesting by the sample processing apparatus 1 or a sample that requires a microscopic examination (step S195). This determination is based on whether the analysis results associated with the rack ID of the sample rack L include retesting information that indicates a necessity of retesting by the sample processing apparatus 1 or retesting information that indicates a necessity of a microscopic examination. At step S195, if the samples held by the sample rack L include a sample that requires retesting by the sample processing apparatus 1 or a sample that requires a microscopic examination (YES at step S195), then the CPU 81*a* determines whether the required retesting (re-measurement) of the sample or smear preparation using the sample can be performed by a measurement unit that is disposed downstream in the transporting direction from the sample transporting apparatus 3 in which the sample rack L is present, or by the smear preparing apparatus 6 (step S196). In this process, whether or not a downstream measurement unit can perform the re-measurement on the sample is determined based on whether or not a measurement item for which the retesting is to be performed is one of the measurement items performable by the downstream measurement unit. For example, if the sample rack L is present in the sample transporting apparatus 3 that is disposed most upstream in the transporting direction among the sample transporting apparatuses, and re-measurement of CBC is necessary for a sample held by the sample rack L, then it is determined that the re-measurement on the sample can be performed by a measurement unit disposed downstream in the transporting direction from the sample transporting apparatus 3, because the measurement units 52 and 53 which are disposed subsequent to the most upstream sample transporting apparatus 3 can perform CBC measurement. On the other hand, if the sample rack L is present in the sample transporting apparatus 3 that is disposed most downstream in the transporting direction among the sample transporting apparatuses, and re-measurement of DIFF is necessary for a sample held by the sample rack L, then it is determined that the re-measurement on the sample cannot be performed by a measurement unit that is disposed downstream in the transporting direction from the sample transporting apparatus 3, because there is no measurement unit disposed subsequent to the sample transporting apparatus 3. Further, if the sample rack L is present in one of the sample transporting apparatuses 3 and a microscopic examination is necessary (i.e., smear preparation is necessary) for a sample held by the sample rack L, it is determined that the smear preparation can be performed by the smear preparing apparatus 6 since the smear preparing apparatus 6 disposed subsequent to the sample transporting apparatuses 3 can perform smear preparation.

When it is determined at step S196 that the required retesting (re-measurement) of the sample or smear preparation using the sample can be performed (YES at step S196), the CPU 81*a* determines a measurement unit that can perform the re-measurement on the sample and that is disposed subsequent to the sample transporting apparatus 3 in which the sample rack L is present, or determines the smear preparing apparatus 6, to be a transportation destination of the sample rack L (step S197). On the other hand, when it is determined at step S196 that the required retesting of the sample or smear preparation using the sample cannot be performed (NO at step S196), the CPU 81*a* determines the sample feeding unit 21 to be a transportation destination of the sample rack L (step S198). The sample rack L, for which the sample feeding unit 21 has been determined to be a transportation destination, is transported to the sample feeding unit 21 via the return line (s). Then, the sample rack L is transported through the pre-processing unit 22 and via the overtaking line(s) again to one of the measurement units 51, 52, and 53 that can perform the re-measurement.

When it is determined at step S195 that the samples held by the sample rack L do not include a sample that requires retesting by the sample processing apparatus 1 or a sample that requires a microscopic examination (NO at step S195), the CPU 81*a* determines whether or not the samples held by the sample rack L include a sample that requires retesting by another apparatus (step S199). In this process, whether or not retesting by another apparatus (a biochemical analyzer, an immune analyzer, a blood coagulation measuring apparatus, or the like) is necessary is determined based on whether or not the analysis results associated with the rack ID of the sample rack L indicate a measurement item for which retesting is necessary and which is different from measurement items performable by the sample processing apparatus 1 (the performable measurement items include CBC, DIFF, and RET) and different from a microscopic examination. At step S199, when the samples held by the sample rack L include a sample that requires retesting by another apparatus (YES at step S199), the CPU 81*a* determines the sample collection unit 24 to be a transportation destination of the sample rack L (step S200). On the other hand, when the samples held by the sample rack L do not include a sample that requires retesting by another apparatus (NO at step S199), the CPU 81*a* determines the sample collection unit 25 to be a transportation destination of the sample rack L (step S201). Accordingly, the sample rack L holding samples that do not include a sample for which a sample bar code reading error has occurred or a sample that requires retesting, is collected by the sample collection unit 25.

After the transportation destination has been determined for the sample rack L in the above manner, the CPU 81*a* transmits, to the sample feeding/collecting apparatus 2, the sample transporting apparatuses 3, and the sample transporting apparatus 4, transportation instruction data which instructs the apparatuses to transport the sample rack L to the determined transportation destination (step S202). Then, the CPU 81*a* ends the processing.

<Second Transporting Operation of Sample Transporting Apparatus 3>

Figure 19:
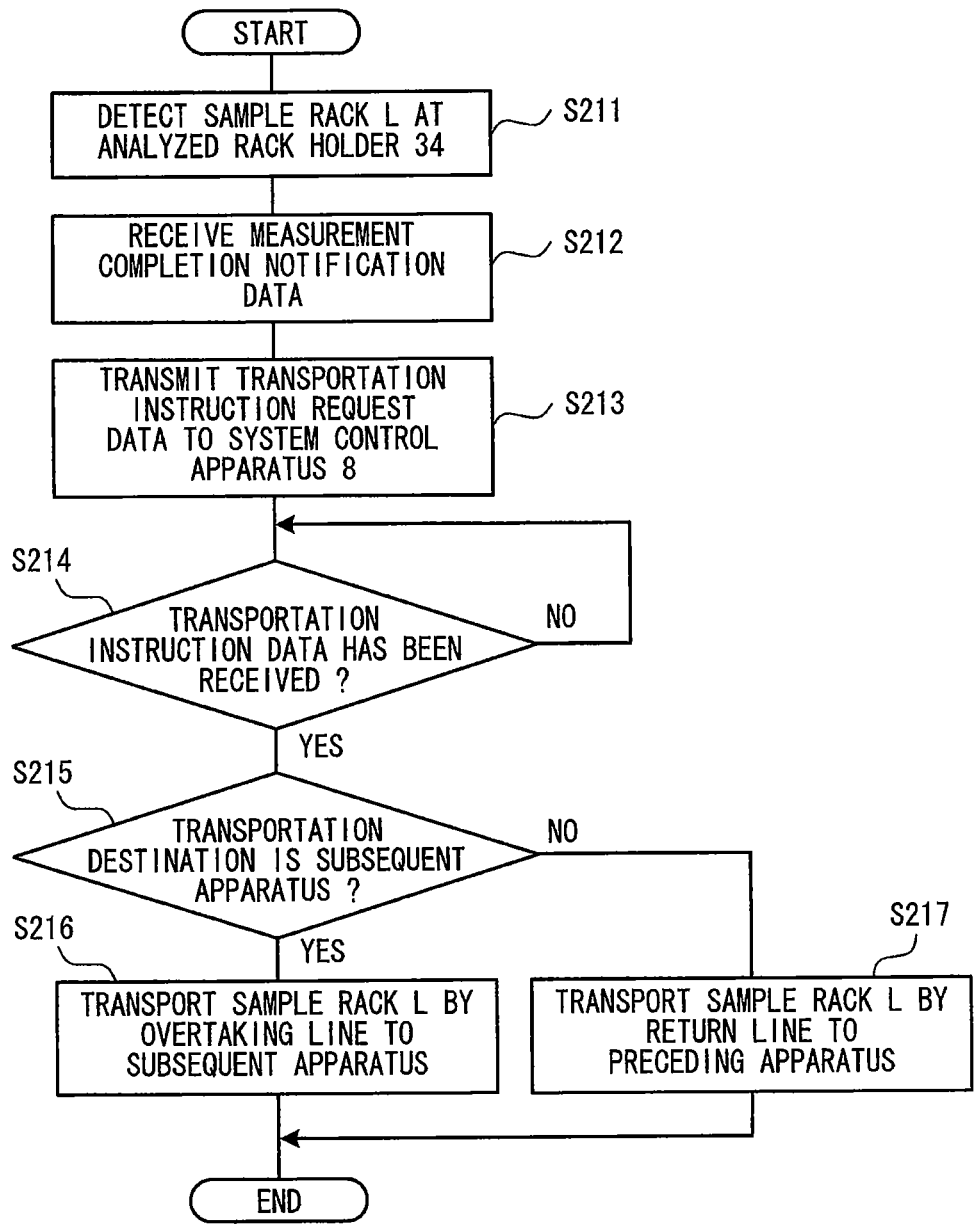
FIG. 19 is a flowchart showing a flow of a second transporting operation performed by each sample transporting apparatus used for the blood analyzer according to the first embodiment.

FIG. 19 is a flowchart showing a flow of a second transporting operation performed by each sample transporting apparatus 3. As described above, when a sample rack L is moved to the analyzed rack holder 34 by the rack send-out part 39 of a sample transporting apparatus 3, the rack sensor detects the sample rack L (step S211). Also, when the sample rack L is moved to the analyzed rack holder 34 by the rack send-out part 39 of the sample transporting apparatus 3, the information processing unit 54 transmits measurement completion notification data that contains the rack ID of the sample rack L to the sample transporting apparatus 3, and the sample transporting apparatus 3 receives the measurement completion notification data (step S212). The controller 32 of the sample transporting apparatus 3 performs the process at step S213 when the rack sensor has detected the sample rack L at the analyzed rack holder 34 and an event of receiving the measurement completion notification data from the information processing unit 54 has occurred.

At step S213, the controller 32 transmits transportation instruction request data that contains the rack ID of the sample rack L to the system control apparatus 8 (step S213). As described above, upon receiving the transportation instruction request data, the system control apparatus 8 determines a transportation destination of the sample rack L, and transmits to the sample transporting apparatus 3 transportation instruction data for transporting the sample rack L to the transportation destination. The controller 32 of the sample transporting apparatus 3 stands by to receive the transportation instruction data (NO at step S214). Upon receiving the transportation instruction data (YES at step S214), the controller 32 determines whether the transportation destination indicated by the transportation instruction data is the smear preparing apparatus 6 or a measurement unit disposed subsequent to the sample transporting apparatuses 3 (step S215). At step S215, when the transportation destination indicated by the transportation instruction data is a subsequent measurement unit or the smear preparing apparatus 6 (YES at step S215), the controller 32 drives the transporting mechanism 31 to move, by means of a rack send-in part 34b, the sample rack L to the rack overtaking transporter 321, and, thereafter, transport the sample rack L, by means of the rack overtaking transporter 321, toward the downstream of the transporting direction so as to send the sample rack L out of the sample transporting apparatus 3 (step S216). Then, the controller 32 ends the processing.

When the sample rack L is transported to the sample transporting apparatus 3 or 4 that corresponds to the subsequent measurement unit or the smear preparing apparatus 6, the sample transporting apparatus 3 or 4 performs the same operation as the first transporting operation of the sample transporting apparatus 3, which has been described with reference to FIG. 14, or the rack transporting operation of the sample transporting apparatus 4, which has been described with reference to FIG. 15, thereby transporting the sample rack L to the transportation destination apparatus.

At step S215, when the transportation destination indicated by the transportation instruction data is not a subsequent measurement unit or the smear preparing apparatus 6, that is, when the transportation destination is one among the sample feeding unit 21 and sample collection units 23, 24, and 25 (NO at step S215), the controller 32 drives the transporting mechanism 31 to move, by means of the rack send-in part 34b, the sample rack L to the rack returning transporter 331 and transport, by means of the rack returning transporter 331, the sample rack L to the preprocessing unit 22 or a sample transporting apparatus 3 that precedes the sample transporting apparatus 3 in which the sample rack L is present (step S217). Then, the controller 32 ends the processing.

If the sample rack L is transported by the rack returning transporter 331 of a sample transporting apparatus 3 that is not disposed most upstream in the transporting direction among the transporting apparatuses 3, or by the rack returning transporter 431 of the sample transporting apparatus 4, to a sample transporting apparatus 3 that is disposed upstream in the transporting direction, then the controller 32 of the sample transporting apparatus 3 to which the sample rack L has been transported drives the rack returning transporter 331 to transport the sample rack L upstream in the transporting direction (i.e., in the X2 direction), thereby transporting the sample rack L to an apparatus disposed further upstream (i.e., a further upstream sample transporting apparatus 3 or the preprocessing unit 22).

<Rack Separate Collection Operation of Sample Feeding/Collecting Apparatus 2>

Figure 20:
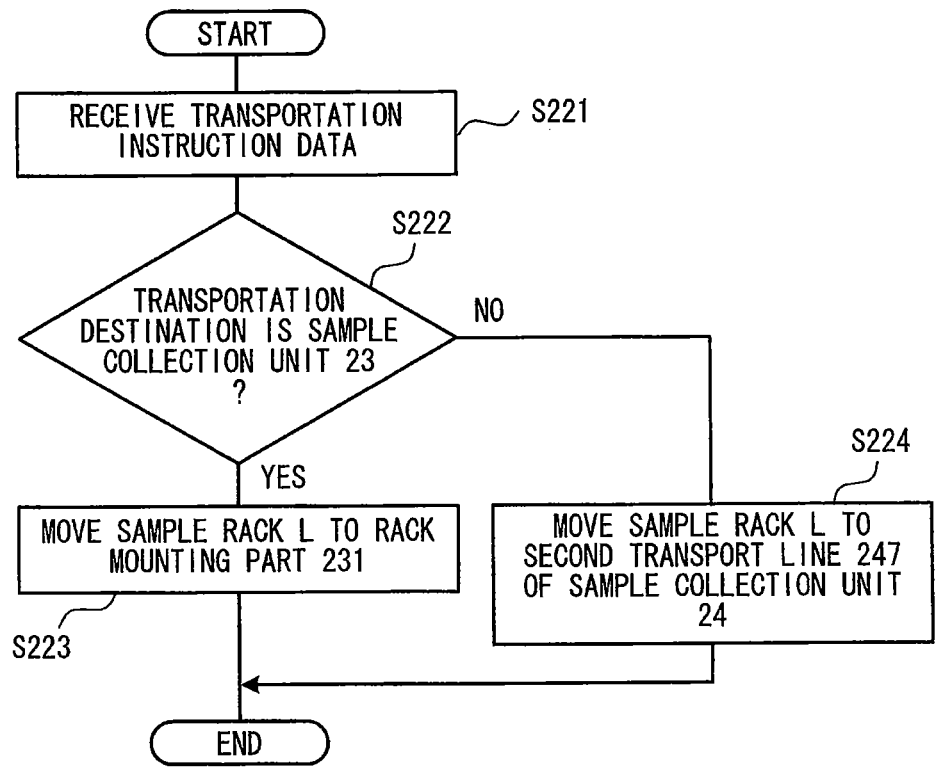
FIG. 20 is a flowchart showing a flow of a rack separate collection operation performed by the sample feeding/collecting apparatus according to the first embodiment.

FIG. 20 is a flowchart showing a flow of a rack separate collection operation performed by the sample feeding/collecting apparatus 2. The rack separate collection operation is performed by each of the controllers of the sample feeding unit 21 and the sample collection units 23 and 24. The rack separate collection operation starts when transportation instruction data as described above is received by the controller from the system control apparatus 8 at step S221. Hereinafter, the rack separate collection operation performed by the controller 23a of the sample collection unit 23 will be described.

Upon receiving transportation instruction data from the system control apparatus 8 (step S221), the controller 23a of the sample collection unit 23 determines based on the transportation instruction data whether or not the transportation destination of a sample rack L that has been transported onto the second transport line 237 via the return line(s), the transport line 223 of the preprocessing unit 22, and the second transport line 217, is the sample collection unit 23 (step S222). When it is determined that the transportation destination is the sample collection unit 23 (YES at step S222), the controller 23a drives the rack moving part 238 to move the sample rack L which has been transported onto the second transport line 237 to the rack mounting part 231 (step S223). Then, the controller 23a ends the processing. In this manner, a sample rack L holding samples that include a sample that has not been measured due to a sample bar code reading error having occurred, is collected by the sample collection unit 23.

As described above, a sample rack L holding a sample for which a sample bar code reading error has occurred is collected by the sample collection unit 23 which is disposed closer to the sample feeding unit 21 than the sample collection units 24 and 25 that collect other sample racks L. It is often the case that a sample rack L that includes a sample for which a sample bar code reading error has occurred is, since the sample has not yet been measured by the measurement unit 51, 52 or 53, fed into the sample feeding unit 21 again after performing a necessary process of eliminating a cause of the sample bar code reading error, for example, removing stains from the sample bar code label BL1 or re-affixing the sample bar code label BL1. Accordingly, as described above, a sample rack L holding a sample for which a sample bar code reading error has occurred is collected by the sample collection unit 23 which is disposed adjacent to the sample feeding unit 21. This allows re-feeding of the sample rack L into the sample feeding unit 21 to be readily performed.

When it is determined at step S222 that the transportation destination is not the sample collection unit 23 (NO at step S222), the controller 23a drives the second transport line 237 to transport the sample rack L upstream in the transporting direction (i.e., in the X2 direction) to the sample collection unit 24, that is, onto the second transport line 247 (step S224).

Each of the sample feeding unit 21 and the sample collection unit 24 is configured to perform the same rack separate collection operation as described above.

To be specific, when the transportation instruction data indicates that the transportation destination of a sample rack L that has been transported onto the second transport line 217 is the sample feeding unit 21, the controller 21a drives the rack moving part 218 to move the sample rack L which has been transported onto the second transport line 217 to the rack mounting part 211. The sample rack L that has been moved to the rack mounting part 211 is sent to the preprocessing unit 22. Processes to be performed thereafter are the same as those of steps S103 to S109 of the above-described sample transporting operation by the sample feeding/collecting apparatus 2, and therefore, the description thereof is omitted.

When the transportation instruction data indicates that the transportation destination of a sample rack L that has been transported onto the second transport line 247 is the sample collection unit 24, the controller 24a drives the rack moving part 248 to move the sample rack L which has been transported onto the second transport line 247 to the rack mounting part 241. In this manner, a sample rack L holding samples that include a sample that requires retesting by another apparatus is collected by the sample collection unit 24.

A sample rack L that has been transported onto the second transport line 257 is moved to the rack mounting part 251 of the sample collection unit 25. In this manner, a sample rack L holding samples that do not include a sample for which a sample bar code reading error has occurred or a sample that requires retesting, is collected by the sample collection unit 25.

Second Embodiment

A second embodiment of the present invention is a sample processing apparatus that includes: a feeding unit for feeding a sample rack that accommodates multiple samples; a preprocessing unit for detecting the amount of each sample held by the sample rack which has been fed, and for detecting the presence or absence of occurrence of coagulation in each sample; transporting apparatuses for transporting the sample rack which has been fed; a blood analyzer; and a first collection unit and a second collection unit for collecting respective sample racks that are transported thereto through the blood analyzer. The sample processing apparatus collects sample racks separately by the first collection unit and the second collection unit in accordance with the amount of each sample held by the sample racks and the presence or absence of occurrence of coagulation in each sample, which are detected by the preprocessing unit.

<Configuration of Sample Processing Apparatus>

Figure 21:
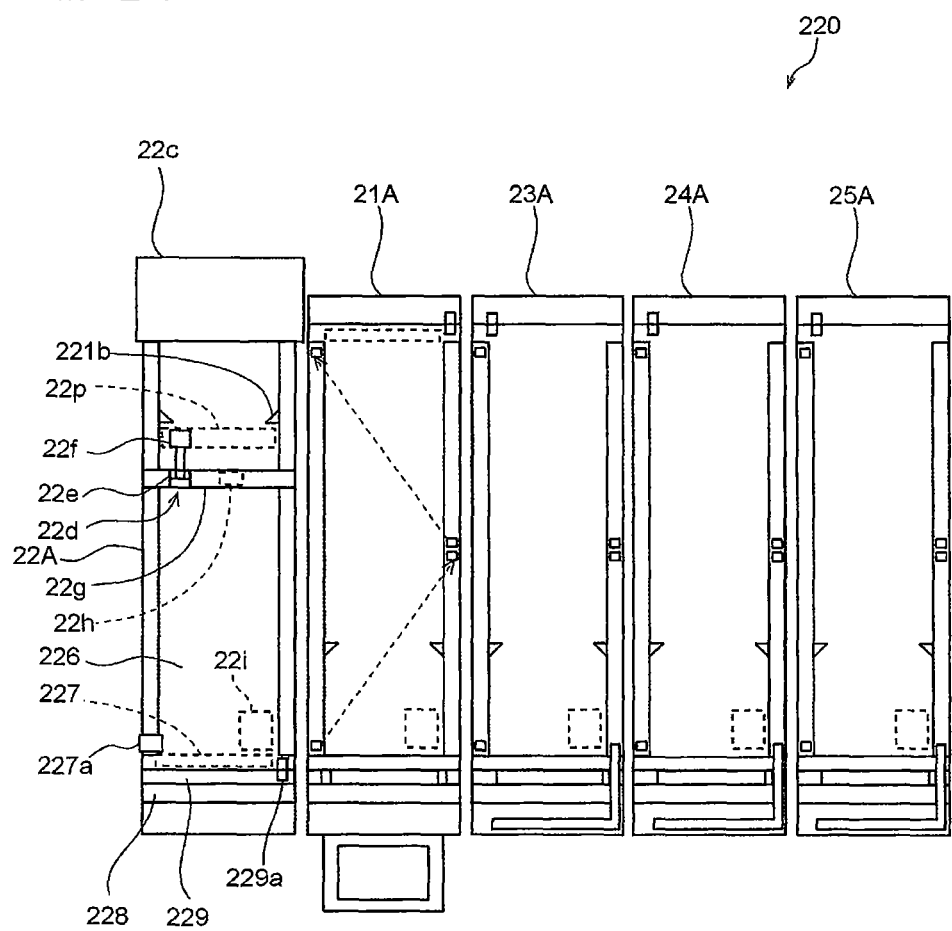
FIG. 21 is a plan view showing a configuration of a sample feeding/collecting apparatus according to a second embodiment.

A sample processing apparatus 210 according to the present embodiment has the same configuration as that of the sample processing apparatus 1 according to the first embodiment, except that a sample feeding/collecting apparatus 220 shown in FIG. 21 is used as a sample feeding/collecting apparatus in the sample processing apparatus 210. Therefore, the components of the sample processing apparatus 210 according to the present embodiment, other than the sample feeding/collecting apparatus 220, will not be described.

<Configuration of Sample Feeding/Collecting Apparatus 220>

FIG. 21 is a plan view showing a configuration of the sample feeding/collecting apparatus 220 according to the present embodiment. As shown in FIG. 21, the sample feeding/collecting apparatus 220 includes a sample feeding unit 21A, a preprocessing unit 22A, and sample collection units 23A, 24A and 25A. The preprocessing unit 22A includes a rack mounting part 226 having a quadrangle shape when seen in plan view. The rack mounting part 226 is configured to accommodate multiple sample racks L. Further, the preprocessing unit 22A includes a bar code reader 22c at the rear side of the rack mounting part 226. The bar code reader 22c is configured to read, at the same time, the sample bar codes of multiple sample containers T accommodated in a sample rack L, and also read the rack bar code of the sample rack L. Since the bar code reader 22c has the same configuration as that of the bar code reader 22b described in the first embodiment, the description thereof is omitted.

The inner surfaces of right and left walls of the rack mounting part 226 have respective engagement portions 221b protruding therefrom. Since the engagement portions 221b of the present embodiment have the same configurations as those of the engagement portions 221a described in the first embodiment, the descriptions thereof are omitted.

The preprocessing unit 22A includes an image-capturing mechanism 22d which is disposed at the front of the bar code reader 22c. The image-capturing mechanism 22d includes: a camera 22e; a holding part 22f configured to hold and move a sample container T in the vertical directions; a moving part 22g for moving the camera 22e and the holding part 22f to the right and left; and an image processing circuit 22h for performing predetermined image processing on an image obtained by the camera 22e. A sample rack L for which sample bar code reading and rack bar code reading have been performed by the bar code reader 22c is moved forward by the engagement portions 221b and arrives at an image capturing position 22p at which the image-capturing mechanism 22d performs image capturing. The image-capturing mechanism 22d is configured to remove a sample container T from the sample rack L located at the image capturing position 22p in the following manner: the holding part 22f grasps the sample container T held by the sample rack L and then moves in the upward vertical direction. The camera 22e captures an image of the sample container T removed from the sample rack L and the image processing circuit 22h performs image processing on the captured image, thereby detecting a liquid surface position of a sample contained in the sample container T and detecting the amount of the sample contained in the sample container T.

After removing the sample container T from the sample rack L, the holding part 22f rotates, at the after-removed position, with respect to the axis extending in the front-rear directions, thereby tilting (rotating) the sample container T. Here, the sample container T is rotated such that the bottom thereof is located at a higher elevation than the head (the cap) thereof. The camera 22e captures an image of the sample container T in such a tilted state. The image processing circuit 22h performs image processing on the image, thereby detecting the presence or absence of coagulation in the sample. To be specific, in the case where sample coagulation (blood coagulation) has occurred, the sample contains aggregated blood cells and has an increased viscosity. Therefore, the image processing circuit 22h detects, through image processing, such an aggregate that protrudes from the liquid surface of the sample or blood that is adhered to the inner wall of the sample container T due to its increased viscosity, thereby detecting the presence of sample coagulation.

In the image-capturing mechanism 22d, the camera 22e and the holding part 22f are moved in a lateral direction so as to sequentially remove, by means of the holding part 22f, sample containers T from the sample rack L and sequentially capture, by means of the camera 22e, images of the sample containers T. In this manner, the process of detecting a sample amount and the process of detecting the presence or absence of sample coagulation are performed for all the sample containers T held by the sample rack L.

The foremost position on the rack mounting part 226 is a rack send-out position 227. The sample rack L, for which the images of all the sample containers T held therein have been captured by the image-capturing mechanism 22d, is moved by the engagement portions 221b to the rack send-out position 227. A transport line 228 which is a belt conveyer is provided at the front of the rack send-out position 227. A wall-like partition 229 protrudes between the transport line 228 and the rack send-out position 227. The partition 229 includes a protruding portion 229a that is movable to the right and left. Since the transport line 228, the partition 229, and the protruding portion 229a have the same configurations as those of the transport line 223, the partition 224, and the protruding portion 225 described in the first embodiment, the descriptions thereof are omitted. The sample rack L having been moved to the rack send-out position 227 is pushed and moved to the left by the protruding portion 229a. Accordingly, the sample rack L is sent out from the preprocessing unit 22 onto the overtaking line of the adjacent sample transporting apparatus.

The preprocessing unit 22A having the configuration as described above includes a controller 22i that includes a CPU, a memory, and the like. The controller 22i controls the mechanics of the preprocessing unit 22A.

The sample feeding unit 21A and the sample collection units 23A, 24A, and 25A according to the present embodiment are the same as the sample feeding unit 21 and the sample collection units 23, 24, and 25 according to the first embodiment, respectively, and therefore, the descriptions thereof are omitted.

<Rack Separate Collection Operation of Sample Feeding/Collecting Apparatus 220>

Samples on which the sample processing apparatus according to the present embodiment is not configured to perform measurement include: a sample for which a sample bar code reading error has occurred; a sample, the detected amount of which is less than a reference amount; and a sample from which blood coagulation has been detected. Sample bar code reading error information indicating an occurrence of a sample bar code reading error, sample amount error information indicating that a detected sample amount is less than the reference amount, and sample coagulation error information indicating that blood coagulation has been detected, are stored in the hard disk of the system control apparatus 8. As with the rack separate collection operation described in the first embodiment, which is performed by the sample feeding/collecting apparatus 2, a sample rack L is collected by one among the sample feeding unit 21A and sample collection units 23A, 24A, and 25A. To be specific, when samples held by a sample rack L include a sample that needs to be retested or a sample for which smear preparation is necessary, the sample rack L is transported to the sample feeding unit 21A; when samples held by a sample rack L include a sample for which a sample bar code reading error, a sample amount error, or a sample coagulation error has occurred, the sample rack L is collected by the sample collection unit 23A; when samples held by a sample rack L include a sample that needs to be retested by another apparatus, the sample rack L is collected by the sample collection unit 24A; and when samples held by a sample rack L do not include any of a sample for which a sample bar code reading error has occurred, a sample for which a sample amount error has occurred, a sample for which a sample coagulation error has occurred, and a sample that needs to be retested, the sample rack L is collected by the sample collection unit 25A.

As described above, a sample rack L that is holding a sample for which a sample bar code reading error, a sample amount error, or a sample coagulation error has occurred is collected by the sample collection unit 23A which is disposed closer to the sample feeding unit 21A than the sample collection units 24A and 25A which collect other sample racks L. It is often the case that a sample rack L holding a sample for which an error as described above has occurred is, since the sample has not yet been measured by a measurement unit, fed into the sample feeding unit 21A again after performing a necessary process of eliminating a cause of the error. Such a process is, for example, removing stains from the sample bar code label BL1 of, or re-affixing a sample bar code label BL1 to, a sample for which a sample bar code reading error has occurred, or diluting a sample for which a sample amount error or a sample coagulation error has occurred. Accordingly, a sample rack L holding a sample for which an error as described above has occurred is collected by the sample collection unit 23A which is disposed adjacent to the sample feeding unit 21A. This allows re-feeding of the sample rack L into the sample feeding unit 21A to be readily performed.

Other Embodiments

The foregoing first and second embodiments describe configurations in which a sample rack L holding a sample that needs to be retested by the sample processing apparatus 1 (210) or holding a sample for which a microscopic examination is necessary, is transported to the sample feeding unit 21 (21A) again, and a sample rack L holding a sample that needs to be retested by another apparatus is collected separately from other sample racks L by the sample collection unit 24 (24A). However, the present invention is not limited thereto. A sample rack L holding a sample that needs to be retested by the sample processing apparatus 1 (210) or holding a sample for which a microscopic examination is necessary, and a sample rack L holding a sample that needs to be retested by another apparatus, may be separately collected by different sample collection units, respectively. In such a case, a sample rack L holding a sample that needs to be retested by the sample processing apparatus 1 (210), and/or a sample rack L holding a sample for which a microscopic examination is necessary, may be collected by a single sample collection unit. This allows an operator of the sample processing apparatus to readily separate, among sample containers T collected by the single sample collection unit, sample containers T containing samples that require retesting or a microscopic examination from sample containers T containing samples that do not require retesting or a microscopic examination, and to readily reset, in a sample rack L, only the sample containers T containing samples that require retesting or a microscopic examination. Consequently, the number of sample racks L to be fed into the sample processing apparatus 1 (210) for sample retesting or smear preparation can be reduced, which contributes to improving the efficiency in transportation of sample racks L. Alternatively, sample racks L holding samples that need to be retested may be collected, separately from other sample racks L, by a single sample collection unit regardless of which of the sample processing apparatus 1 (210) and another apparatus performs the retesting.

However, the collection of sample racks L need not be separated into the collection of sample racks L each accommodating samples including a sample that requires retesting and the collection of sample racks L each accommodating samples, none of which require retesting. Alternatively, the collection of sample racks L may be separated into the collection of sample racks L each accommodating samples including a sample in which an abnormality has been detected as a result of sample analysis and the collection of sample racks L each accommodating samples in none of which an abnormality has been detected. Still alternatively, sample racks L may be separately collected according to the types of abnormalities detected in samples held by the sample racks L (e.g., "increased red blood cells" and "abnormality in platelet particle size distribution").

If there is a sample rack L accommodating a sample that has not been measured or for which smear preparation has not been performed due to malfunction of the measurement unit 51, 52, 53, or the smear preparing apparatus 6, then the sample rack L may be collected by a sample collection unit that is disposed closer to the sample feeding unit 21 than the other sample collection units that collect other sample racks L. It is often the case that a sample that has not been measured or for which smear preparation has not been performed due to malfunction of a measurement unit or the smear preparing apparatus is fed into the sample feeding unit 21 after the measurement unit or the smear preparing apparatus has recovered from the malfunction. Therefore, a sample rack L accommodating a sample that has not been measured or for which smear preparation has not been performed due to malfunction of a measurement unit or the smear preparing apparatus is collected by a sample collection unit disposed near the sample feeding unit 21. This allows re-feeding of the sample rack L into the sample feeding unit 21 to be readily performed.

In the above-described embodiments, sample racks L are separately collected in such a manner that the computer 8a of the system control apparatus 8 determines destinations where the sample racks L are to be collected, and based on the determined destinations, the controller of each sample collection unit controls the operations of its rack moving part and second transport line. However, the present invention is not limited thereto. Sample racks L may be separately collected in such a manner that the process of determining destinations where the sample racks L are to be collected and the process of controlling the operations of the rack moving parts and the second transport lines are performed by a single computer (controller).

The second embodiment describes a configuration in which the preprocessing unit 22A performs sample bar code reading, sample amount detection, and sample coagulation presence/absence detection. However, the present invention is not limited thereto. In addition to such preprocessing or in place of a part or the whole of such preprocessing, detection of the amount of chyle contained in a sample may be performed. When the detected amount of chyle is equal to or greater than a predetermined value, it is determined that a chyle error has occurred and the sample is not measured, accordingly. A sample rack L accommodating a sample for which a chyle error has occurred may be collected separately from other sample racks L.

Further, the second embodiment describes a configuration in which among sample racks L, only a sample rack L accommodating a sample that has not been measured due to an occurrence of a sample bar code reading error, a sample amount error, or a sample coagulation error, is collected by the sample collection unit 23 and thereby separated from the other sample racks L. However, the present invention is not limited thereto. Alternatively, sample racks L may be separately collected according to the types of errors (e.g., a sample bar code reading error, a sample amount error, and a sample coagulation error). When a sample bar code reading error has occurred, it is necessary to remove stains from the bar code label or re-affix the bar code label, for example. When a sample amount error has occurred, it is necessary to dilute the sample, for example. When a sample coagulation error has occurred, it is necessary to discard the sample, for example. Thus, a necessary process is different for each error. Therefore, the alternative collection manner as described above allows an operator of the sample processing apparatus to perform the same process on multiple samples at the same time, for which the same error has occurred. This improves the efficiency of work that is performed after the collection of sample racks L.

Although the preprocessing unit 22 is disposed next to the sample feeding unit 21 in the above-described embodiments, the present invention is not limited thereto. For example, a sample amount check sensor may be provided in each sample transporting apparatus 3, and sample racks L may be separately collected according to check results provided by the sample amount check sensors.

The above-described embodiments describe configurations in which the sample processing apparatus 1 includes the blood cell analyzer 5 that classifies blood cells in a sample into their respective types and counts each type of blood cells. However, the present invention is not limited thereto. The sample processing apparatus may be configured to include a sample analyzer different from a blood cell analyzer, such as an immune analyzer, a blood coagulation measuring apparatus, a biochemical analyzer, or a urine analyzer, and transport a blood sample or urine sample to a measurement unit of the sample analyzer.

Although the above-described embodiments describe configurations in which the blood cell analyzer 5 includes three measurement units 51, 52, and 53, and the information processing unit 54, the present invention is not limited thereto. The number of measurement units may be either one or more. Moreover, the measurement units and the information processing unit may be integrated. Furthermore, the mechanics of the measurement units 51, 52, and 53 need not be controlled by the information processing unit 54. Each measurement unit may include a controller that includes a CPU, a memory, and the like. Each measurement unit may be controlled by the controller included therein. The information processing unit may process measurement data obtained by the measurement units, and thereby generate sample analysis results.

Further, the above-described embodiments describe configurations in which the single computer 8a executes all the processes according to the computer program 84a. However, the present invention is not limited thereto. The same processes as the above-described processes according to the computer program 84a may be executed by multiple apparatuses (computers) in a distributed manner (i.e., a distributed system).

Still further, the above-described embodiments describe configurations in which the sample processing apparatus 1 (210) includes the sample feeding/collecting apparatus 2 (220), the sample transporting apparatuses 3 and 4, the blood cell analyzer 5, the smear preparing apparatus 6, and the system control apparatus 8. However, the present invention is not limited thereto. As an alternative configuration, a blood analyzer may include: one or more measurement units; an information processing unit; a transporting unit for transporting a sample rack L; and a preprocessing unit such as a bar code reader. In the blood analyzer, sample racks L accommodating sample containers T on which preprocessing by the preprocessing unit has been performed are transported through the measurement unit(s) by the transporting unit. The sample racks L are separately collected according to, for example, preprocessing results or sample analysis results.

What is claimed is:

1. A sample processing apparatus comprising:
   a row of transporting units, each of the transporting units comprising an upstream line that transports sample containers in an upstream direction and a downstream line that transports the sample containers in a downstream direction, wherein each upstream line of each transporting unit is laterally aligned to form an upstream transport path and each downstream line of each transporting unit is laterally aligned to form a downstream transport path;

a row of measurement units that measures samples contained in the sample containers, wherein the row of measurement units corresponds to the row of transporting units;

an information processing unit that processes measurement data outputted from the measurement units and outputs an analysis result of the samples contained in the sample containers, wherein the analysis result includes a result of determination as to whether or not re-measuring the samples is necessary;

a plurality of container collection units that collect respective sample containers transported by the row of transporting units, each container collection unit comprising a first upstream transport line that is laterally aligned with the upstream transport path and laterally transports the sample containers in the upstream direction;

a container feeding unit that feeds the sample containers to the row of transporting units, wherein the container feeding unit is located between the container collection units and the row of transporting units and comprises a second upstream transport line; and a preprocessing unit comprising a reader that reads identification information of a selected sample from an identifier associated with a selected sample container holding the selected sample, wherein the preprocessing unit is arranged side by side with the container feeding unit and comprises a second downstream transport line that is laterally aligned with the downstream transport path and laterally transports the sample containers in the downstream direction;

wherein the container feeding unit comprises a side wall including an open portion through which a sample rack is transported to the preprocessing unit; and wherein the container feeding unit, the container collection units, and the transporting units are connected such that the second upstream transport line of the container feeding unit is laterally aligned with the first upstream transport lines of the container collection units and the upstream transport path such that the sample containers are seamlessly transported to a collection destination in the upstream direction.

2. The sample processing apparatus of claim 1, further comprising:

a collection controller programmed to control the row of transporting units to transport the sample containers to the collection destination via the upstream transport path, wherein the collection destination specifies one of the container collection units for each sample container based on the result of determination as to whether or not re-measuring the samples is necessary;

wherein the plurality of container collection units includes a first container collection unit for collecting sample containers having properly tested samples and a second container collection unit for collecting sample contains having samples which require re-measuring by another sample processing apparatus.

3. The sample processing apparatus of claim 2, wherein each transporting unit is configured to transport a sample rack holding multiple sample containers, and the collection controller is programmed to control, according to the analysis result of the samples in the sample containers, each transporting unit such that the sample rack is collected in one of the container collection units.

4. The sample processing apparatus of claim 2, wherein the collection controller comprises: a first controller that determines, for the sample containers transported by the row of transporting units, the collection destination at which the sample containers are to be collected; and a second controller that controls, based on the collection destination determined by the first controller, collection operations of the plurality of container collection units.

5. The sample processing apparatus of claim 4, wherein each of the container collection units comprises a placement part on which each sample container is to be placed and a moving part for moving each sample container to the placement part, and the second controller controls an operation of the moving part based on the collection destination determined by the first controller.

6. The sample processing apparatus of claim 2, wherein the plurality of container collection units are arranged side by side in the downstream direction.

7. The sample processing apparatus of claim 2, wherein the collection controller is programmed to control the row of the transporting units such that when the analysis result indicates that re-measuring a sample is not necessary, the collection controller controls the row of the transporting units so as to transport a sample container holding the sample to the first container collection unit.

8. The sample processing apparatus of claim 7, wherein the collection controller is programmed to control the row of the transporting units such that when an analysis result indicates that re-measuring a sample is required, the collection controller controls the row of the transporting units so as to transport a sample container holding the sample to the second container collection unit.

9. The sample processing apparatus of claim 8, wherein the collection destination specifies one of the first container collection unit and the second container collection unit.

10. The sample processing apparatus of claim 8, wherein the collection destination specifies a container collection unit other than the first container collection unit and the second container collection unit.

11. The sample processing apparatus of claim 1, wherein:
the container collection units comprise a first container collection unit and a second container collection unit, and the first container collection unit is disposed closer to the transporting units than the second container collection unit such that the sample containers received from the transporting units are transported via the first upstream transport line of the first container collection unit to the second container collection unit and the second container collection unit receives the sample containers from the first upstream transport line of the first container collection unit.

12. The sample processing apparatus of claim 11, wherein the first container collection unit comprises a first placement part on which the sample containers are to be placed and a first moving part for moving the sample containers transported via the first upstream transport line to the first placement part, wherein the first moving part is configured to slide the sample containers toward the first placement part.

* * * * *